United States Patent [19]

Sakuma et al.

[11] Patent Number: 5,378,700

[45] Date of Patent: Jan. 3, 1995

[54] FUSED PYRIMIDINE DERIVATIVE, PROCESS FOR PREPARATION OF SAME AND PHARMACEUTICAL PREPARATION COMPRISING SAME AS ACTIVE INGREDIENT

[75] Inventors: Yasuji Sakuma; Masaichi Hasegawa; Kenichiro Kataoka; Kenji Hoshina, all of Hino; Noboru Yamazaki; Takashi Kadota, both of Hachioji; Hisao Yamaguchi, Hino, all of Japan

[73] Assignee: Teijin Limited, Osaka, Japan

[21] Appl. No.: 839,769

[22] PCT Filed: Oct. 11, 1990

[86] PCT No.: PCT/JP90/01313

§ 371 Date: Jun. 9, 1992

§ 102(e) Date: Jun. 9, 1992

[87] PCT Pub. No.: WO91/05784

PCT Pub. Date: May 2, 1991

[30] Foreign Application Priority Data

Oct. 11, 1989 [JP] Japan .................. 1-264763

[51] Int. Cl.[6] .................. C07D 471/04; C07D 487/04; A61K 31/505; A61K 31/55

[52] U.S. Cl. .................. 514/212; 514/215; 514/218; 514/228.5; 514/234.2; 514/258; 540/544; 540/553; 540/575; 540/578; 540/597; 540/603; 544/61; 544/127; 544/143; 544/279; 544/280

[58] Field of Search .......... 514/212, 215, 218, 228.5, 514/234.2, 258; 540/544, 553, 575, 578, 597, 603; 544/279, 280, 61, 127, 143

[56] References Cited

U.S. PATENT DOCUMENTS

3,631,045 12/1971 Kim .................. 544/200

OTHER PUBLICATIONS

Bitter et al. *Heterocycles* 23, 1167 (1985).
Takahata *Synthesis* pp. 226-228 (1983).
"An Investigaton of Lactams X: Chemical Synthesis of 9H, Pynimido [4, 5-b] azepin Derivatives from Caprolactam", V. G. Granik, R. G. Grucikof *Khim Pharm Zh* 1(5), 21–26 (1967) (with partial translation).

*Primary Examiner*—Mark L. Berch
*Attorney, Agent, or Firm*—Sughrue, Mion, Zinn, Macpeak & Seas

[57] ABSTRACT

Disclosed is a fused pyrimidine of the formula [I]

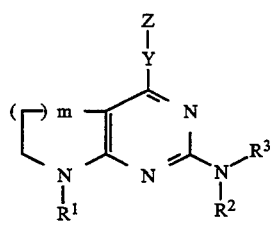

wherein $R^1$, $R^2$, and $R^3$ are as defined in the specification,

Y represents a linking group of the formula

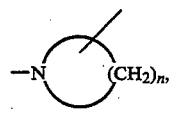

wherein n is an integer of from 4 to 6,

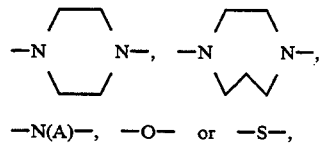

—N(A)—, —O— or —S—, wherein A is a hydrogen atom or alkyl group; and
Z represents a hydrogen atom, or other substituents; or Y and Z together represent an unsubstituted or substituted alkyl, alkenyl or arylalkyl group; or a 5- to 7-member heterocyclic ring which has a nitrogen atom, and further, an oxygen or sulfur atom as (Abstract continued on next page.)

a hetero atom other than the nitrogen atom, being bonded via the nitrogen atom therein to the 4-position of the pyrimidine ring of the formula (I), a 5- to 7-member unsaturated heterocyclic ring which has 1 to 3 nitrogen atoms being bonded via the nitrogen atom therein to the 4-position of the pyrimidine ring of the formula (I), or a fused biheterocyclic ring constructed with 5- or 6-membered aromatic or non-aromatic rings, which has 1 to 3 nitrogen atoms in any position, being bonded via the nitrogen atom therein to the 4-position of the pyrimidine ring of the formula (I); and m is an integer of from 1 to 3;

and a pharmaceutically acceptable acid addition salt thereof, as well as a process for producing same and a pharmaceutical preparation useful for a treatment of hypoxemia associated with respiratory diseases.

8 Claims, No Drawings

FUSED PYRIMIDINE DERIVATIVE, PROCESS FOR PREPARATION OF SAME AND PHARMACEUTICAL PREPARATION COMPRISING SAME AS ACTIVE INGREDIENT

TECHNICAL FIELD

The present invention relates to a novel fused pyrimidine derivative, in particular, a fused pyrimidine derivative having a substituted amino group at the 2- position of the pyrimidine ring and a substituted amino, oxy, thio, alkyl, alkenyl or arylalkyl group at the 4- position of the pyrimidine ring, and a pharmaceutically acceptable acid addition salt thereof. Further, the invention relates to a pharmaceutical preparation comprising said derivative or said pharmaceutically acceptable acid addition salt, as an active ingredient.

BACKGROUND ART

Among fused pyrimidine compounds, 5,6-dihydro-7H-pyrrolo[2,3-d]pyrimidine derivatives having an amino group at their 2- and 4-positions and a process for producing these compounds are known in the art [see, Yamazaki et al., *Synthesis*, Vol. 3, 266 (1983)]. Similarly, 5,6,7,8-tetrahydropyrido[2,3-d]pyrimidine derivatives having an amino group at their 2- and 4-positions are known in the art [see, Ibid.; and I. Bitter et al., *Heterocycles*, Vol. 23, 1167 (1985)]. Further, 5,6,7,8-tetrahydro-9H-pyrimido[4,5-b]azepine derivatives having an amino group at their 2- and 4-positions are also known in the art [see, R. G. Glushkov et al., *Khim. -Farm. Zh.*, Vol. 1, 21 (1967)]. Nevertheless, biological activities of these fused pyrimidines have not been known in the art.

Further, no fused pyrimidine derivatives having a substituted amino group at the 2-position of the pyrimidine ring and a substituted amino, oxy, thio, alkyl, alkenyl or arylalkyl group at its 4-position at the same time, has been disclosed in the prior art, and it is not known that the same have a specific pharmacologic activity.

DISCLOSURE OF THE INVENTION

Our extensive and intensive researches on the fused pyrimidine derivatives resulted in a discovery of the compound defined as the general formula [I] described below which have an excellent pharmacologic activity against hypoxemia associated with respiratory diseases.

Note, the present inventors, in related research, found that some pyrrolo[2,3-d]pyrimidine derivatives have the same pharmacologic activity as the compounds of the present invention, have filed a patent application, which is copending, prior to the filing of this application.

Accordingly, in accordance with the present invention, novel fused pyrimidine derivatives having the general formula [I] described below, and pharmaceutically acceptable acid addition salts thereof, and a process for preparation of the same and pharmaceutical preparations comprising a compound selected from the same, are provided:

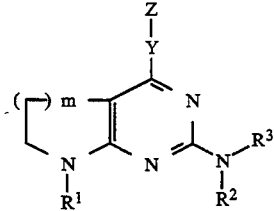

wherein
$R^1$ represents a hydrogen atom, or an unsubstituted or substituted alkyl, alkenyl, arylalkyl, arylalkenyl or alkylcarbonyl group;
$R^2$ and $R^3$, independently of each other, represent a hydrogen atom, or an unsubstituted or substituted alkyl, alkenyl, arylalkyl, arylalkenyl or alkylcarbonyl group; or $R^2$ and $R^3$ are optionally taken together with the adjacent nitrogen atom to form a saturated 5- to 7-membered ring, which may be constructed with at least one hetero atom selected from N, O and S, with the proviso that either $R^2$ or $R^3$ represents a group other than a hydrogen atom;
Y represents a linking group of the formula

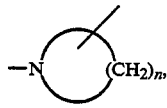

wherein n is an integer of from 4 to 6,

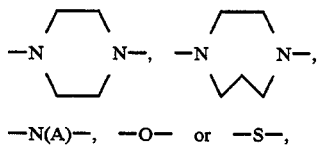

—N(A)—, —O— or —S—, wherein A is a hydrogen atom or alkyl group; and
Z when bonded to a carbon atom on said linking group, represents a hydrogen atom, or carboxylic, amino or hydroxyl group, or an unsubstituted or substituted alkyl, aryl, arylalkyl, alkyloxy, alkylcarbonyloxy, alkyloxycarbonyl, arylcarbonyloxy, arylalkylcarbonyloxy, arylalkenylcarbonyloxy, alkylamino, alkenylamino, arylamino, arylalkylamino or alkylcarbonylamino group; and when bonded to an atom other than said carbon atom of the linking group and represents a hydrogen atom, or an unsubstituted or substituted alkyl, alkenyl, aryl, arylalkyl, arylalkenyl, alkylcarbonyl, arylalkylcarbonyl, arylalkenylcarbonly or arylcarbonyl group; or Y and Z together represent an unsubstituted or substituted alkyl, alkenyl or arylalkyl group; or a 5- to 7- member heterocyclic ring which has a nitrogen atom, and further, an oxygen or sulfur atom as a hetero atom other than the nitrogen atom, being bonded via the nitrogen atom therein to the 4-position of the pyrimidine ring of the formula [I], a 5- to 7- member unsaturated heterocyclic ring which has 1 to 3 nitrogen atoms, being bonded via a nitrogen atom therein to the 4-position of the pyrimidine ring of the general formula [I], or a fused biheterocyclic ring which has 1 to 3 nitrogen atoms in any position, being bonded via the nitrogen atom therein to the 4-position of the pyrimidine ring of the formula [I];

m is an integer of from 1 to 3; and
in said substituted alkyl, alkenyl, aryl, arylalkyl, arylalkenyl, alkylcarbonyl, arylcarbonyl, arylalkylcarbonyl, arylalkenylcarbonyl, alkylcarbonyloxy, alkyloxy-carbonyl, arylcarbonyloxy, arylalkylcarbonyloxy, arylalkenylcarbonyloxy, alkylamino, arylamino, arylalkylamino and alkylcarbonylaminos groups, the substituent represents an alkyl, halogenated alkyl, alkyloxy, alkylcarbonyloxy, hydroxyl, amino, nitro or cyano group, or a halogen atom, which is bonded to chain or ring moiety in said substituted groups, or an alkylene group taken together with a carbon atom in the chain moiety to form a ring.

BEST MODE OF CARRYING OUT THE INVENTION

The present invention is disclosed in detail below.

An alkyl group or alkyl moiety of each group, unless defined otherwise, includes a $C_1$–$C_{10}$ straight or branched chain aliphatic hydrocarbon, alicyclic hydrocarbon or cyclic-chain aliphatic hydrocarbon residue. Preferably, the alkyl group or the alkyl moiety includes a $C_1$–$C_6$ straight or branched alkyl group, a $C_3$–$C_7$ cyclic alkyl group and a $C_3$–$C_6$ cyclic—$C_1$–$C_3$ chain alkyl group. Specific examples of such group are methyl, ethyl, propyl, isopropyl, butyl, isobutyl, secbutyl, tertbutyl, pentyl, hexyl, cyclopropyl, cyclobutyl, cyclopentyl, cyclohexyl, cyclopropylmethyl, cyclobutylmethyl, cyclohexylmethyl and the like.

The alkenyl group or alkenyl moiety of each group, unless otherwise defined, includes a $C_3$–$C_6$ straight or branched chain aliphatic hydrocarbon, which has a double bond. Specific examples of such group are 1-propenyl, allyl, 1-methylallyl, 2-methylallyl, 1-butenyl, 2-butenyl, 2-methyl-2-butenyl, 3-methyl-2-butenyl, 3-butenyl, 2-pentenyl, 3-methyl-2-pentenyl, 2-hexenyl, 3-cyclopropylally, 3-cyclopentenyl, 3-cyclohexyenyl, and the like.

The aryl group or aryl moiety of each group includes an aromatic hydrocarbon cyclic or heterocyclic group constructed of 5- or 6- membered monocyclic or fused ring. Specific examples of such group are phenyl, 1-naphthyl, 2-naphthyl, 2-pyrrolyl, 2-furyl, 2-thienyl, 2-pyridyl, etc., and in particular, phenyl, 1-naphthyl and 2-naphthyl, are preferred.

Accordingly, the arylalkyl group in accordance with the invention is intended to mean the alkyl group bonded to said aryl moiety, and preferably a $C_1$–$C_6$ straight or branched chain alky bonded to the aryl moiety. Specific examples of such groups are benzyl, 1-phenylethyl, 1-methyl-1-phenylethyl, 2-phenylethyl, 3-phenylpropyl, diphenylmethyl, triphenylmethyl, 1-naphthylmethyl, 1-(1-naphthy)ethyl, 1,2,3,4-tetrahydronaphtharen-1-yl, 2-pyrrolylmethyl, 2-furfuryl, 2-thienylmethyl, and the like.

The arylalkenyl group includes the alkenyl group bonded to said aryl moiety, and preferably a $C_3$–$C_6$ alkenyl group bonded to said aromatic hydrocarbone. Of these, in particular, the cinnamyl group, etc., is preferred.

The alkylcarbonyl group includes the carbonyl group bonded to said alkyl moiety, and preferably a $C_2$–$C_7$ alkylcarbonyl group. Specific examples of such groups are acetyl, propanoyl, butanoyl, 2-methylpropanoyl, pentanoyl, 2-methylbutanoyl, 3-methylbutanoyl, pivaloyl, hexanoyl, cyclopropylcarbonyl, and the like.

The arylcarbonyl group includes the carbonyl group bonded to said aryl moiety, such as benzoyl, toluoyl, naphthoyl, 2-pyrrolecarbonyl, 2-furoyl, 2-thiophenecarbonyl, and the like.

The arylalkylcarbonyl group includes the carbonyl group bonded to said arylalkyl moiety, such as phenyl acetyl, 3-phenylpropanoyl, 4-phenylbutanoyl, diphenylacetyl, naphthylacetyl, 2-pyrrolylacetyl, 2-furylacetyl, 2-thienylacetyl, and the like.

The arylalkenylcarbonyl group includes the carbonyl group bonded to said arylalkenyl moiety, and particularly, cinnamoyl, etc. is preferred.

The alkylcarbonyloxy or arylcarbonyloxy group includes each oxygen atom bonded to said alkylcarbonyl or arylcarbonyl moiety, respectively, such as acetoxy, propanoyloxy, butanoyloxy, 2-methylpropanoyloxy, pentanoyloxy, pivaloyloxy, hexanoyloxy, and the like; and benzoyloxy, toluoyloxy, naphthoyloxy, 2-pyrrolecarbonyloxy, 2-furoyloxy, 2-thiophenecarbonyloxy, and the like.

Further, the arylalkyl- or arylalkenyl-carbonyloxy group includes each oxygen atom bonded to said arylalkylcarbonyl or arylalkenylcarbonyl moiety, respectively, such as phenylacetoxy, 3-phenylpropanoyloxy, 4-phenylbutanoyloxy, cinnamoyloxy, 2-pyrrolylacetoxy, 2-furylacetoxy, 2-thienylacetoxy, and the like.

The alkyloxy group, which is constructed of said alkyl moiety and oxy group, includes, for example, methoxy, ethoxy, propoxy, butoxy, isopropoxy, cyclopropylmethyloxy, and the like.

The alkyloxycarbony group includes a group in which a carbonyl group is bonded via an oxygen atom to said alkyl moiety, and is, for example, methoxycarbonyl, ethoxycarbonyl, propoxycarbonyl, isopropoxycarbonyl, butoxycarbony, and the like.

The alkylamino group, alkenylamino group, arylamino group, arylalkylamino group and alkylcarbonylamino group are amino groups in which the hydrogen atom of the amino groups is substituted by said alkyl group(s), alkenyl group(s), aryl group(s), arylalkyl group(s) and alkylcarbonyl groups(s), respectively, and includes, for example, methylamino, ethylamino, propylamino, allylamino, dimethylamino, diethylamino, anilino, benzylamino, 1-phenylethylamino, 2-phenylethylamino, diphenylmethylamino, acetamide, propanamide, and the like.

In the substituted alkyl, alkenyl, aryl, arylalkyl, arylalkenyl, alkylcarbonyl, arylcarbonyl, arylalkylcarbonyl, arylalkenylcarbonyl, alkylcarbonyloxy, alkyloxycarbonyl, arylcarbonyloxy, arylalkylcarbonyloxy, arylalkenylcarbonyloxy, alkylamino, alkenylamino, arylamino, arylalkylamino and alkylcarbonylamino, the substituent represents a $C_1$–$C_4$ alkyl, halogenated $C_1$–$C_4$ alkyl, $C_1$–$C_4$ alkyloxy, $C_1$–$C_5$ alkylcarbonyloxy, hydroxyl, nitro, cyano or amino group, or halogen atom, e.g., fluorine, chlorine, bromine or iodine atom, which is or are bonded to a chain or ring moiety; or an $\alpha$, $\omega$-alkylene group, which is taken together with a carbon atom in an alkyl chain moiety to form a ring, having e.g.,

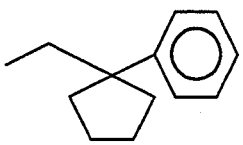

as the substituted form.

According to the above-described definitions, the $R^1$ in the formula [I] represents a hydrogen atom or an unsubstituted or substituted alkyl, alkenyl, arylalkyl, arylalkenyl or alkylcarbonyl group. Suitable specific examples of the alkyl group include methyl, ethyl, propyl, isopropyl, butyl, cyclopropyl, cyclopropylmethyl, trifluoromethyl, methoxymethyl, methoxyethoxymethyl, 2-aminoethyl, and the like. Suitable specific examples of the alkenyl group include allyl, 2-methylallyl, 2-butenyl, 3-methyl-2-butenyl, 2-fluoroallyl, 2-(trifluoromethyl)allyl, 3-butenyl, and the like. Suitable specific examples of the arylalkyl group include benzyl, 4-fluorobenzyl, 4-chlorobenzyl, 3-(trifluoromethyl)benzyl, 4-methoxybenzyl, 2-phenylethyl, 2-[(2-trifluoromethyl)phenyl]ethyl, triphenylemthyl, (4-methoxyphenyl)diphenylmethyl, 2-thienylmethyl, and the like. Suitable specific examples of the allkenyl groups include cinnamyl, and the like. Suitable specific examples of the alkylcarbonyl group include acetyl, trifluoroacetyl, propanoyl, 2-methylpropanoyl, butanoyl, and the like.

The $R^2$ and $R^3$ in formula [I] are identical with definitions of the $R^1$, respectively, and suitable examples thereof as well are identical with those of $R^1$. The $R^2$ and $R^3$ are optionally taken together with an adjacent nitrogen atom to form a saturated 5- to 7-membered ring, which may be constructed with at least one hetero atom (for example, N, O or S) in its ring other than the above-described nitrogen. Suitable specific examples of the saturated 5- to 7- membered ring group include 1-pyrrolidinyl, piperidino, 1-piperazinyl, 4-[bis(4-fluorophenyl)methyl]-1-piperazinyl, morpholino, thiomorpholino, 1-perhydro[1,4]diazepinyl, and the like.

The group having the formula —Y—Z in the formula [I] consists of a linking group which represents the formula:

wherein n is an integer of from 4 to 6,

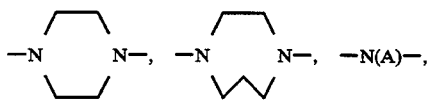

wherein A is a hydrogen atom or alkyl group, —O— or —S—, and a group as specifically disclosed below.

Of the groups having the formula

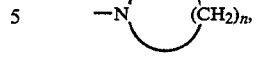

wherein n is as defined above, in particular, groups of the formula

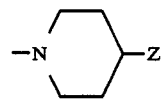

are preferred, suitable specific examples of the group Z include a hydrogen atom; an alkyl group, such as methyl, propyl, cyclohexyl, and the like; an aryl group, such as phenyl, 1-naphthyl, 2-naphthyl, 4-fluorophenyl, and the like; an arylalkyl group, such as benzyl, 4-fluorobenzyl, 4-metoxybenzyl, 4-nitrobenzyl, and the like; an alkylcarbonyloxy group, such as acetoxy, propanoyloxy, 2-methylpropanoyloxy, and the like; an alkyloxy group, such as methoxy, ethoxy, propoxy, isopropoxy, and the like; alkyloxycarbonyl, such as methoxycarbonyl, ethoxycarbonyl, propoxycarbonyl, isopropoxycarbonyl, and the like; an arylcarbonyloxy group, such as benzoyloxy, naphthoyloxy, 2-furoyloxy, 2-thiophenecarbonyloxy, and the like; an arylalkyl- or arylalkenylcarbonyloxy group, such as phenylacetoxy, 4-nitrophenylacetoxy, 3-phenylpropanoyloxy, cinnamoyloxy, and the like; an alkyl-, alkenyl-, aryl-, arylalkyl- or alkylcarbonyl- amino group, such as methylamino, ethylamino, butylamino, allylamino, 2-methylallylamino, anilino, benzylamino, bis(4-fluorophenyl)methyl amino, acetamide, and the like; a carboxyl group, and a hydroxyl group.

In particular, in the groups of the formulae

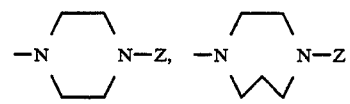

and —N(A)—Z, suitable specific examples of Z include an unsubstituted or substituted alkyl group, such as methyl, ethyl, propyl, isopropyl, butyl, cyclopropyl, cyclopropylmethyl, cyclohexyl, trifluoromethyl, methoxymethyl, 2-methoxyethyl, 2-hydroxyethyl, 2-aminoethyl, and the like; an unsubstituted or substituted alkenyl group, such as ally, 2-methylally, 2-butenyl, 3-methyl-2-butenyl, 2-fluoroallyl, 2-(trifluoromethyl)allyl, 3-butenyl, 3-cyclohexenyl, and the like; an unsubstituted or substituted aryl group, such as phenyl, 1-naphthyl, 2-naphthyl, 2-pyrrolyl, 2-furyl, 2-thienyl, 4-fluorophenyl, 4-chlorophenyl, 4-trifluoromethylphenyl, and the like; an unsubstituted or substituted arylalkyl or arylalkenyl group, such as benzyl, 4-fluorobenzyl, 4-chlorobenzyl, 3-(trifluoromethyl)benzyl, 4-methoxybenzyl, 4-cyanobenzyl, triphenylmethyl, (4-methoxyphenyl)diphenylmethyl, bis(4-fluorophenyl)methyl, diphenylmethyl, 1-phenylethyl, 1-methyl-1-phenylethyl, 2-phenylethyl, 2-[2-(trifluoromethyl)phenyl]ethyl, 2-(2-nitrophenyl)ethyl, 2-(4-chlorophenyl)ethyl, 2-(4-methoxyphenyl- )ethyl, 2-(4-hydroxyphenyl)ethyl, 2-(4-fluorophenyl-)ethyl, 2,2-(α,ω-butanediyl)-2-phenylethyl:

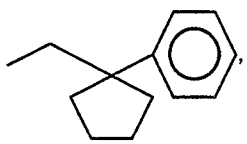

fluorophenyl)-2,2-(α,ω-butanediyl)ethyl, 2,2-diphenylethyl, 3-phenylpropyl, 1-(1-naphthyl)ethyl, 1,2,3,4-tetrahydronaphthalene-1-yl, 2-pyrrolylmethyl, 2-furfuryl, 2-thienylmethyl, cinnamyl, and the like; an unsubstituted or substituted alkylcarbonyl group, such as acetyl, trifluoroacetyl, propanoyl, 2-methylpropanoyl, butanoyl, pivaloyl and the like; an arylalkyl- or arylalkenyl-carbonyl group, such as phenylacetyl, 3-phenylpropanoyl, cinnamoyl, and the like; and an arylcarbonyl, such as benzoyl, naphthoyl, 2-furoyl, 2-thiophenecarbonyl, and the like, wherein said A is a hydrogen atom, methyl, ethyl or propyl. Further, in particular, suitable specific examples of the Z as described in the formula —O—Z and —S—Z, include an unsubstituted or substituted alkyl group, such as methyl, ethyl, propyl, isopropyl, butyl, cyclopropyl, cyclopropylmethyl, cyclohexyl, trifluoromethyl, methoxymethyl, 2-methoxyethyl, 2-hydroxyethyl, 2-aminoethyl, and the like; an unsubstituted or substituted alkenyl, such as allyl, 2-methylallyl, 2-butenyl, 3-methyl-2-butenyl, 2-fluoroallyl, 2-(trifluoromethyl)allyl, 3-butenyl, and the like; an unsubstituted or substituted aryl group, such as phenyl, 1-naphthyl, 2-naphthyl, 2-pyrrolyl, 2-furyl, 2-thienyl, 4-fluorophenyl, 4-chlorophenyl, 4-trifluoromethylphenyl, and the like; and an unsubstituted or substituted arylalkyl or arylalkenyl, such as benzyl, 4-fluorobenzyl, 4-chlorobenzyl, 3-(trifluoromethyl)-benzyl, 4-methoxybenzyl, triphenylmethyl, (4-methoxyphenyl)diphenylmethyl, 1-methyl-l-phenylethyl, bis(4-fluorophenyl)methyl, diphenylmethyl, 1-phenylethyl, 2-phenylethyl, 2-[2-(trifluoromethyl)phenyl]ethyl, 2-(4-chlorophenyl)ethyl, 2-(4-methoxyphenyl)methyl, 2-(4-fluorophenyl)ethyl, 2,2-(α,ω-butandiyl)-2-phenylethyl, [2-(4-fluorophenyl)-2,2-(α,ω-butandiyl)]ethyl, 2-pyrrolylmethyl, 2-frufuryl, 2-thienylmethyl, cinnamyl, and the like.

Further, when Y and Z together are an unsubstituted or substituted alkyl, alkenyl or arylalkyl group, or heterocyclic ring residue, which are bonded via a nitrogen atom to the 4-position on the pyrimidine ring of the formula [I], these groups (or residues) include an unsubstituted or substituted groups, such as ethyl propyl, butyl, hexyl, 1-propenyl, 1-butenyl, 2-phenylethyl, 2-[2-(trifluoromethyl)phenyl]ethyl, 2-(4-chlorophenyl)ethyl, 2-(4-methoxyphenyl)methyl, 2-(4-fluorophenyl)ethyl, and the like, and a heterocyclic ring group having the following formulae:

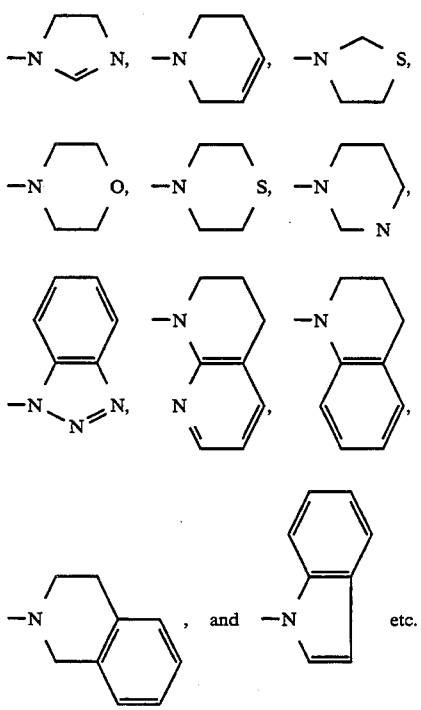

Suitable specific examples of fused pyrimidine derivative of the general formula [I] in accordance with the present invention include the compounds containing the substituents described in the following table. Note, when the compound has asymmetric carbon atoms in the structure thereof, the compounds of the present invention include all optical isomers.

| Compound No. | R¹ | R² | R³ | Y | Z | m |
|---|---|---|---|---|---|---|
| 101 | $CH_3$ | H | ![but-2-enyl] | 4-methylpiperidin-1-yl | OAc | 1 |
| 102 | $CH_3$ | H | ![but-2-enyl] | —NH— | ![but-3-enyl] | 1 |
| 103 | ![but-2-enyl] | H | ![but-2-enyl] | pyrrolidin-2-yl | H | 1 |
| 104 | ![but-2-enyl] | H | ![but-2-enyl] | —N(CH$_3$)— | $CH_3$ | 1 |
| 105 | Ac | H | ![but-2-enyl] | piperazin-1-yl | $F_2BH$ | 1 |
| 106 | H | H | benzyl (o-ethyl) | 4-methylpiperidin-1-yl | 4-nitrophenylacetate | 1 |
| 107 | H | H | $CH_3$ | piperazin-1-yl | $F_2BH$ | 2 |
| 108 | H | H | $CH_3$ | piperazin-1-yl | $F_2BH$ | 2 |

Formula [I]: structure with Z—Y—[pyrimidine with N, N=C(R²)NR³, and N-R¹ ring of size m]

Note: R³ column for compound 108 shows a butenyl group.

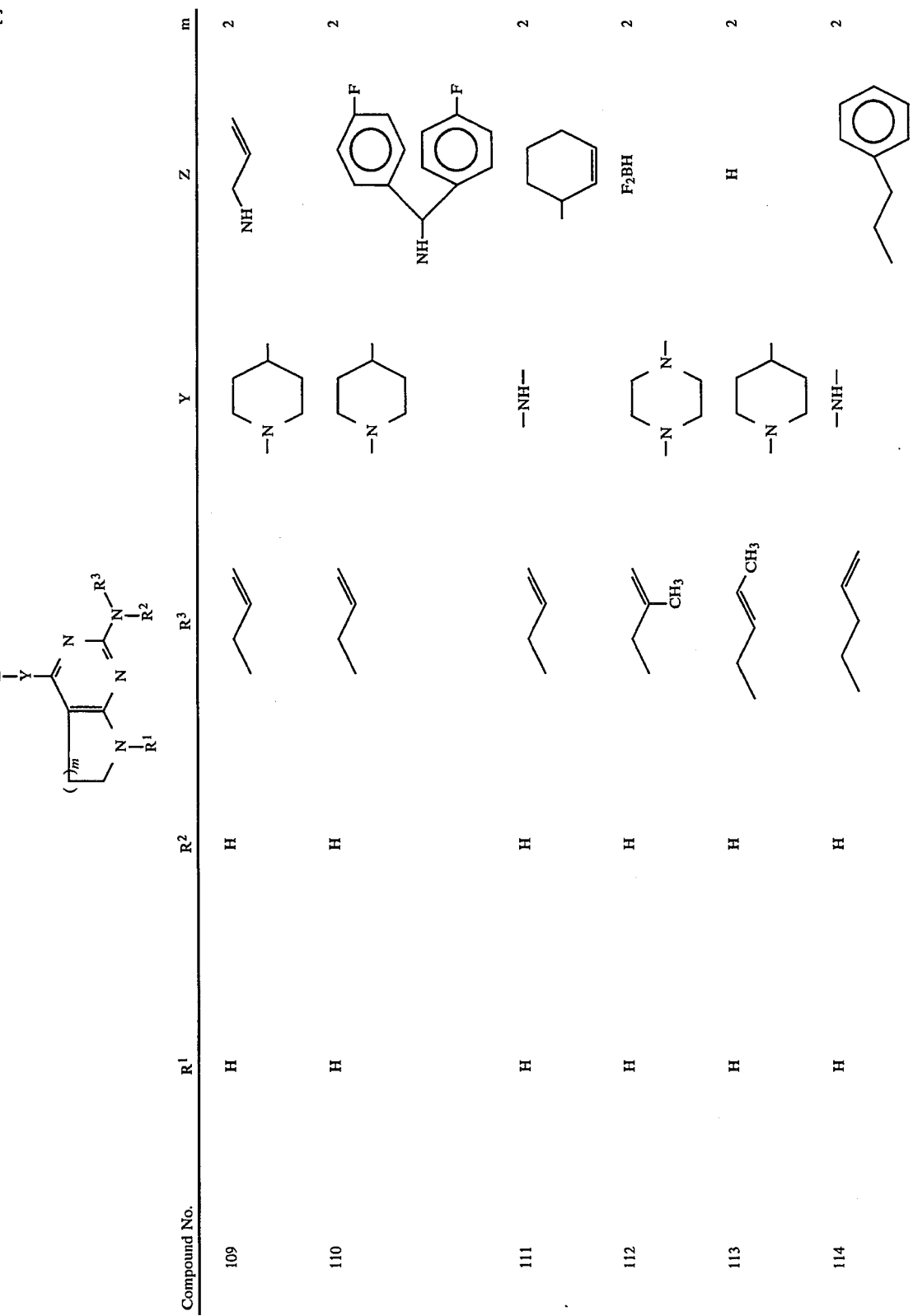

-continued

[I]

| Compound No. | R¹ | R² | R³ | Y | Z | m |
|---|---|---|---|---|---|---|
| 115 | H | H | | 4-methylpiperidinyl | cyclohexyl | 2 |
| 116 | H | H | (CH₃)₃C-C(=O)- | 4-methylpiperidinyl | NHAc | 2 |
| 117 | CH₃ | H | -CH₂-O-CH₂-CH₂- | N-methylpiperazinyl | F₂BH | 2 |
| 118 | CH₃ | H | CH₃ | 2-methylpyrrolidinyl | CO₂H | 2 |
| 119 | CH₃ | H | CH₂CH=CHCH₃ | 4-methylpiperidinyl | CO₂iPr | 2 |
| 120 | CH₃ | H | CH₂CH=CHCH₃ | N-methylpiperazinyl | F₂BH | 2 |
| 121 | CH₃ | H | CH₂CH=CHCH₃ | —NH— | CH₂CH=CHCH₃ | 2 |

-continued

[Structure I: pyrimidine fused with N-R¹ containing ring, with (CH₂)ₘ, substituents Z-Y- and -N=C(R²)(R³)]

| Compound No. | R¹ | R² | R³ | Y | Z | m |
|---|---|---|---|---|---|---|
| 122 | CH₃ | H | cyclohex-2-enyl | —NH— | cyclohex-2-enyl | 2 |
| 123 | CH₃ | H | but-2-enyl | —S— | but-2-enyl | 2 |
| 124 | CH₃ | H | 2-fluoro-pent-1-enyl | —NH— | propylphenyl | 2 |
| 125 | CH₃ | H | hex-1-enyl | piperazinyl | pent-1-enyl | 2 |
| 126 | CH₃ | H | cyclohex-2-enyl | —NH— | F₂BH | 2 |
| 127 | CH₃ | H | styryl-propyl | | but-2-enyl | 2 |
| 128 | CF₃ | H | MMTr | piperazinyl | CH₃ | 2 |
| 129 | CH₃ | H | Ac | piperazinyl | F₂BH | 2 |

[I]

-continued
[I]
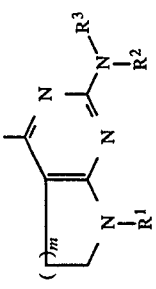
| Compound No. | R¹ | R² | R³ | Y | Z | m |
|---|---|---|---|---|---|---|
| 130 | CH₃-CH₂-CH₂- | H | -CH₂-CH=CH- | piperazinyl (N-Me) | F₂BH | 2 |
| 131 | CH₃-CH₂-CH₂- | H | Ac | piperazinyl (N-Me) | F₂BH | 2 |
| 132 | cyclopropyl-CH₂- | H | cyclopropyl-CH₂- | piperazinyl (N-Me) | CH₃ | 2 |
| 133 | cyclopropyl-CH₂- | H | cyclohexyl-CH₂- | piperazinyl (N-Me) | 2-acetylthienyl | 2 |
| 134 | cyclopropyl-CH₂- | H | -CH₂-CH=CH- | piperazinyl (N-Me) | F₂BH | 2 |
| 135 | cyclopropyl-CH₂- | H | -CH₂-CH=CH- | —NH— | 4-chlorobenzyl | 2 |

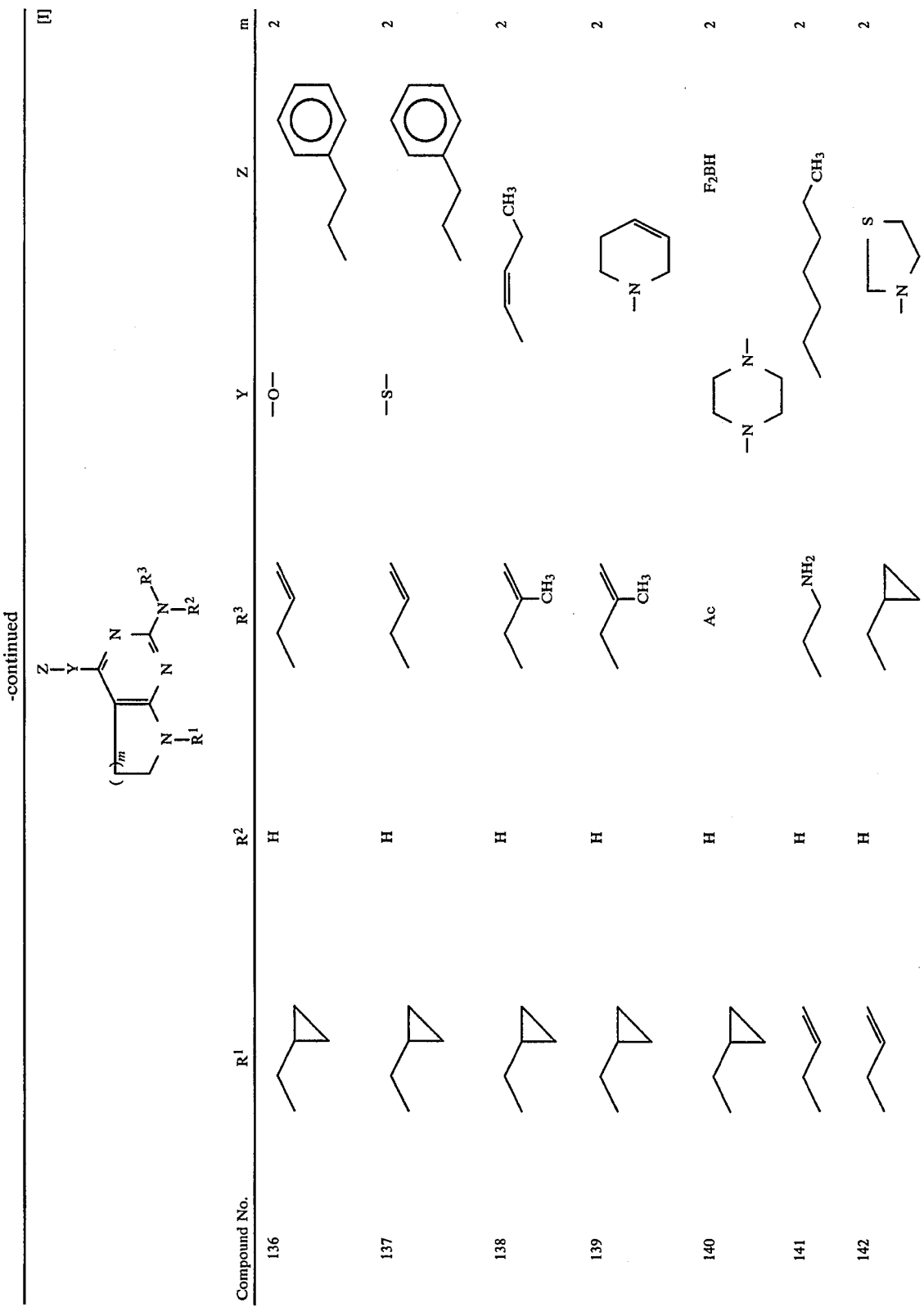

-continued

[I]

| Compound No. | R¹ | R² | R³ | Y | Z | m |
|---|---|---|---|---|---|---|
| 143 | but-2-enyl | H | but-2-enyl | N-methylpyrrolidin-2-yl | H | 2 |
| 144 | but-2-enyl | H | but-2-enyl | N-methylpyrrolidin-2-yl | benzyl | 2 |
| 145 | but-2-enyl | H | but-2-enyl | 1-methylpiperidin-4-yl | H | 2 |
| 146 | but-2-enyl | H | but-2-enyl | 1-methylpiperidin-4-yl | phenyl | 2 |
| 147 | but-2-enyl | H | but-2-enyl | 1-methylpiperidin-4-yl | OH | 2 |
| 148 | but-2-enyl | H | but-2-enyl | 1-methylpiperidin-4-yl | OAc | 2 |

-continued

[I] structure: pyrazolo-pyrimidine-like core with substituents Z-Y-, R³R²N-, R¹-N, and (CH₂)m ring.

| Compound No. | R¹ | R² | R³ | Y | Z | m |
|---|---|---|---|---|---|---|
| 149 | CH₂CH=CHCH₃ | H | CH₂CH₂CH=CHCH₃ | 1-methylpiperidin-4-yl | 4-chlorobenzoyloxy | 2 |
| 150 | CH₂CH=CHCH₃ | H | CH₂CH₂CH=CHCH₃ | 1-methylpiperidin-4-yl | bis(4-fluorophenyl)methylamino | 2 |
| 151 | CH₂CH=CHCH₃ | H | CH₂CH₂CH=CHCH₃ | 1-methylpiperidin-4-yl | NH.Ac | 2 |
| 152 | CH₂CH=CHCH₃ | H | CH₂CH₂CH=CHCH₃ | 1,2-dimethylpiperidinyl | phenyl | 2 |
| 153 | CH₂CH=CHCH₃ | H | CH₂CH₂CH=CHCH₃ | 1-methylazepan-yl | H | 2 |

-continued [I]

| Compound No. | R¹ | R² | R³ | Y | Z | m |
|---|---|---|---|---|---|---|
| 154 | CH₂CH=CHCH₃ | H | CH₂CH=CHCH₃ | piperazine | H | 2 |
| 155 | CH₂CH=CHCH₃ | H | CH₂CH=CHCH₃ | piperazine | CH₃ | 2 |
| 156 | CH₂CH=CHCH₃ | H | CH₂CH=CHCH₃ | piperazine | CH₂CH₃ | 2 |
| 157 | CH₂CH=CHCH₃ | H | CH₂CH=CHCH₃ | piperazine | 4-F-C₆H₄ | 2 |
| 158 | CH₂CH=CHCH₃ | H | CH₂CH=CHCH₃ | piperazine | 3-F-4-ethylphenyl | 2 |
| 159 | CH₂CH=CHCH₃ | H | CH₂CH=CHCH₃ | piperazine | F₂BH | 2 |
| 160 | CH₂CH=CHCH₃ | H | CH₂CH=CHCH₃ | piperazine | CH=CHC₆H₅ (styryl) | 2 |

-continued

| Compound No. | R¹ | R² | R³ | Y | Z | m |
|---|---|---|---|---|---|---|
| 161 | CH₂CH=CHCH₃ | H | CH₂CH=CHCH₃ | piperazine | -CH=CH-C(O)-C₆H₅ | 2 |
| 162 | CH₂CH=CHCH₃ | H | CH₂CH=CHCH₃ | piperazine | -CH=CH-C(O)-C₆H₄-Cl | 2 |
| 163 | CH₂CH=CHCH₃ | H | CH₂CH=CHCH₃ | homopiperazine | CH₃ | 2 |
| 164 | CH₂CH=CHCH₃ | H | CH₂CH=CHCH₃ | -NH- | H | 2 |
| 165 | CH₂CH=CHCH₃ | H | CH₂CH=CHCH₃ | -NH- | CH₃ | 2 |
| 166 | CH₂CH=CHCH₃ | H | CH₂CH=CHCH₃ | -NH- | CH₂CH₂OCH₃ | 2 |
| 167 | CH₂CH=CHCH₃ | H | CH₂CH=CHCH₃ | -NH- | CH₂CH₂NH₂ | 2 |
| 168 | CH₂CH=CHCH₃ | H | CH₂CH=CHCH₃ | -NH- | CH₂CH=CHCH₃ | 2 |

-continued

[I] (structure shown with R¹, R², R³, Y, Z, m substituents on a fused bicyclic pyrimidine system)

| Compound No. | R¹ | R² | R³ | Y | Z | m |
|---|---|---|---|---|---|---|
| 169 | propyl | H | propenyl | —NH— | phenyl | 2 |
| 170 | propyl | H | propenyl | —NH— | benzyl | 2 |
| 171 | propyl | H | propenyl | —NH— | phenylpropyl | 2 |
| 172 | propyl | H | propenyl | —NH— | 4-Cl-phenylpropyl | 2 |
| 173 | propyl | H | propenyl | —NH— | 4-OCH₃-phenylpropyl | 2 |
| 174 | propyl | H | propenyl | —NH— | 4-OH-phenylpropyl | 2 |
| 175 | propyl | H | propenyl | —NH— | phenylbutyl | 2 |

-continued

[I]

(structure: pyrrolo-pyrimidine with Z-Y-, R³/R² on amino, R¹ on N, (CH₂)ₘ ring)

| Compound No. | R¹ | R² | R³ | Y | Z | m |
|---|---|---|---|---|---|---|
| 176 | CH₂CH=CHCH₃ | H | CH₂CH=CHCH₃ | —NH— | 1-ethyl-1-phenylcyclopentyl | 2 |
| 177 | CH₂CH=CHCH₃ | H | CH₂CH=CHCH₃ | —NH— | 1-ethyl-1-(4-fluorophenyl)cyclopentyl | 2 |
| 178 | CH₂CH=CHCH₃ | H | CH₂CH=CHCH₃ | —NH— | 1,1-diphenylpropyl | 2 |
| 179 | CH₂CH=CHCH₃ | H | CH₂CH=CHCH₃ | —NH— | 1-methyl-1-phenyl | 2 |

-continued

[I]

| Compound No. | R¹ | R² | R³ | Y | Z | m |
|---|---|---|---|---|---|---|
| 180 | CH₂CH=CHCH₃ | H | CH₂CH=CHCH₃ | —NH— | 1-methyl-1,2,3,4-tetrahydronaphthyl | 2 |
| 181 | CH₂CH=CHCH₃ | H | CH₂CH=CHCH₃ | —NH— | C(CH₃)₂-phenyl | 2 |
| 182 | CH₂CH=CHCH₃ | H | CH₂CH=CHCH₃ | —NH— | 1-(1-naphthyl)ethyl | 2 |
| 183 | CH₂CH=CHCH₃ | H | CH₂CH=CHCH₃ | —NH— | C(=O)-phenyl | 2 |
| 184 | CH₂CH=CHCH₃ | H | CH₂CH=CHCH₃ | —N(CH₃)— | CH₃ | 2 |
| 185 | CH₂CH=CHCH₃ | H | CH₂CH=CHCH₃ | —N(CH₃)— | CH₂CH₃ | 2 |
| 186 | CH₂CH=CHCH₃ | H | CH₂CH=CHCH₃ | —N(CH₃)— | CH₂CH₂CH₂OH | 2 |

-continued
[I]
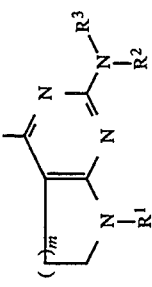
| Compound No. | R¹ | R² | R³ | Y | Z | m |
|---|---|---|---|---|---|---|
| 187 | propenyl | H | propenyl | —N(CH$_3$)— | —CH$_2$CH$_2$CH$_3$ | 2 |
| 188 | propenyl | H | propenyl | —N(CH$_3$)— | —CH$_2$CH=CH$_2$ | 2 |
| 189 | propenyl | H | propenyl | —N(CH$_3$)— | —CH$_2$—C$_6$H$_5$ | 2 |
| 190 | propenyl | H | propenyl | —N(CH$_3$)— | —CH$_2$—C$_6$H$_4$-F | 2 |
| 191 | propenyl | H | propenyl | —N(CH$_3$)— | —CH$_2$—C$_6$H$_4$-CN | 2 |
| 192 | propenyl | H | propenyl | —N(CH$_3$)— | —CH$_2$CH$_2$—C$_6$H$_5$ | 2 |
| 193 | propenyl | H | propenyl | —N(CH$_3$)— | —CH$_2$CH$_2$—C$_6$H$_4$-NO$_2$ | 2 |

-continued

[I]

| Compound No. | R¹ | R² | R³ | Y | Z | m |
|---|---|---|---|---|---|---|
| 194 | CH₂CH=CHCH₃ | H | CH₂CH=CHCH₃ | —N(CH₃)— | 2-CF₃-C₆H₄ | 2 |
| 195 | CH₂CH=CHCH₃ | H | CH₂CH=CHCH₃ | —N(CH₂CH₃)— | C₆H₅CH(CH₃)— | 2 |
| 196 | CH₂CH=CHCH₃ | H | CH₂CH=CHCH₃ | —O— | CH₃ | 2 |
| 197 | CH₂CH=CHCH₃ | H | CH₂CH=CHCH₃ | —O— | CH₂CH=CHCH₃ | 2 |
| 198 | CH₂CH=CHCH₃ | H | CH₂CH=CHCH₃ | —O— | C₆H₅CH₂CH₂— | 2 |
| 199 | CH₂CH=CHCH₃ | H | CH₂CH=CHCH₃ | —S— | CH₃ | 2 |
| 200 | CH₂CH=CHCH₃ | H | CH₂CH=CHCH₃ | —S— | cyclohexyl | 2 |
| 201 | CH₂CH=CHCH₃ | H | CH₂CH=CHCH₃ | —S— | CH₂CH=CHCH₃ | 2 |

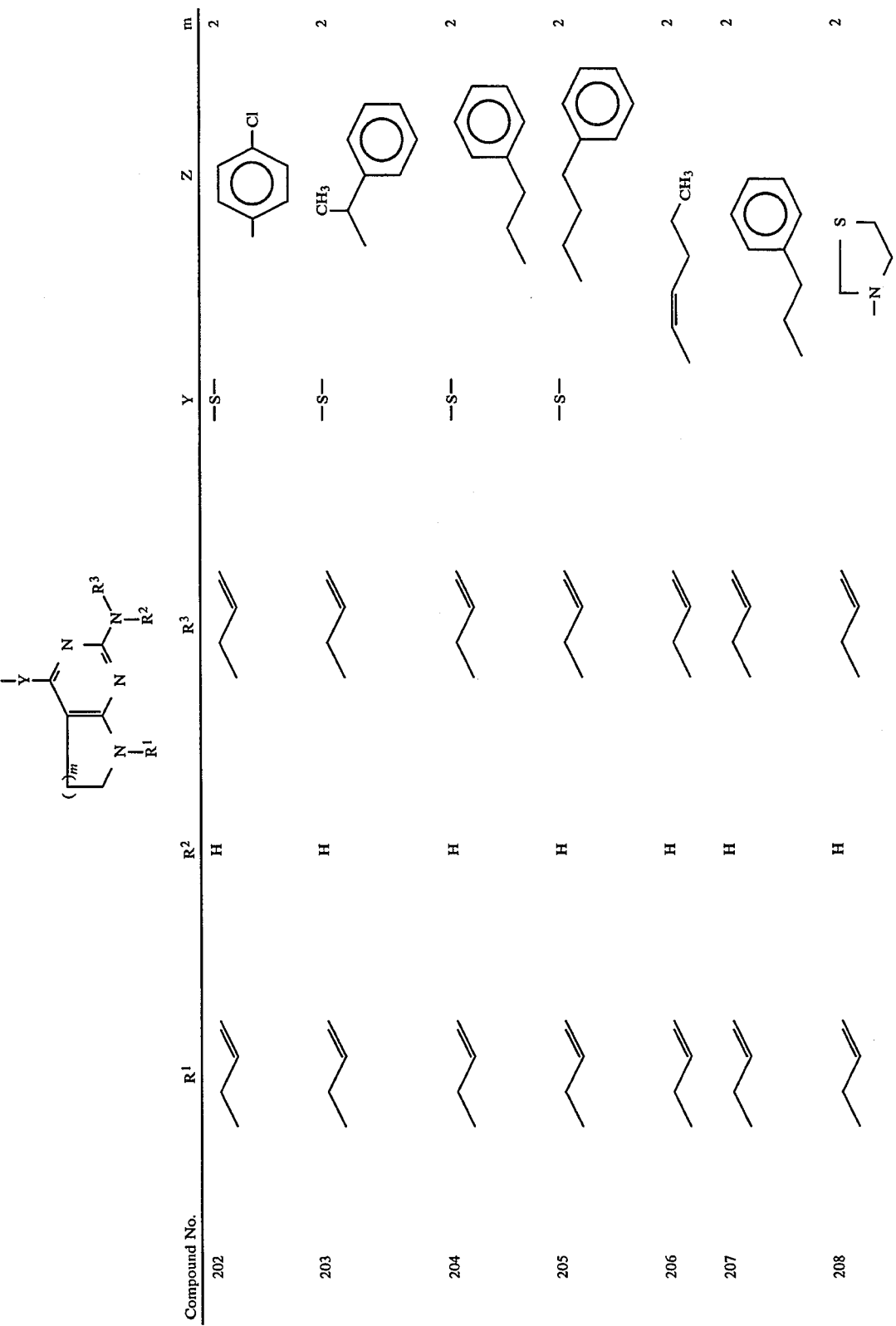

-continued

[I]

| Compound No. | R¹ | R² | R³ | Y | Z | m |
|---|---|---|---|---|---|---|
| 209 | *propyl* | H | *propyl* | | morpholine (O) | 2 |
| 210 | *propyl* | H | *propyl* | | thiomorpholine (S) | 2 |
| 211 | *propyl* | H | *propyl* | | imidazole | 2 |
| 212 | *propyl* | H | *propyl* | | tetrahydropyrimidine | 2 |
| 213 | *propyl* | H | *propyl* | | tetrahydropyridine | 2 |
| 214 | *propyl* | H | *propyl* | | tetrahydroisoquinoline | 2 |

-continued
[I]
| Compound No. | R¹ | R² | R³ | Y | Z | m |
|---|---|---|---|---|---|---|
| 215 | 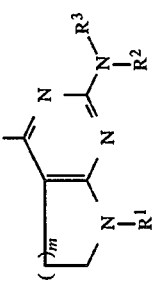 | H | (but-2-enyl) | | (benzotriazol-1-yl) | 2 |
| 216 | (but-2-enyl) | H | Ac | (piperazin-1-yl, N-Me) | $F_2BH$ | 2 |
| 217 | (but-2-enyl) | $CH_3$ | (but-2-enyl) | (piperazin-1-yl, N-Me) | $F_2BH$ | 2 |
| 218 | (but-2-enyl) | (but-2-enyl) | (but-2-enyl) | (piperazin-1-yl, N-Me) | $F_2BH$ | 2 |
| 219 | (but-2-enyl) | (but-2-enyl) | (but-2-enyl) | (4-Me-piperidin-1-yl) | $\text{–CH}_2\text{CH}_2\text{CH}_2\text{–Ph}$ | 2 |
| 220 | (2-methylbut-2-enyl) | H | (but-2-enyl) | (4-Me-piperidin-1-yl) | $NH–CH_2CH_3$ | 2 |

-continued

[I]

| Compound No. | R¹ | R² | R³ | Y | Z | m |
|---|---|---|---|---|---|---|
| 221 | CH₂CH=C(CH₃)– (2-methylbut-2-enyl) | H | CH₂CH=CHCH₃ | 4-methylpiperidin-1-yl | OAc | 2 |
| 222 | CH₂CH=C(CH₃)– | H | CH₂CH=CHCH₃ | piperazin-1-yl (N-methyl) | Ac | 2 |
| 223 | CH₂CH=C(CH₃)– | H | CH₂CH=CHCH₃ | piperazin-1-yl (N-methyl) | F₂BH | 2 |
| 224 | CH₂CH=C(CH₃)– | H | CH₂C(CH₃)=CHCH₃ | piperazin-1-yl (N-methyl) | F₂BH | 2 |
| 225 | CH₂CH=C(CH₃)– | H | CH₂C(CH₃)=CHCH₃ | –NH– | –(CH₂)₃OCH₃ | 2 |
| 226 | CH₂CH=C(CH₃)– | H | CH₂C(CH₃)=CHCH₃ | –NH– | CH₂C(CH₃)=CHCH₃ | 2 |
| 227 | CH₂CH=C(CH₃)– | H | CH₂C(CH₃)=CHCH₃ | –NH– | 2-(CF₃)-6-propylphenyl | 2 |

-continued

[I]

| Compound No. | R¹ | R² | R³ | Y | Z | m |
|---|---|---|---|---|---|---|
| 228 | CH₂=C(F)CH₂CH₃ | H | CH₂=C(F)CH₂CH₃ | piperazine (N–N) | CH₃ | 2 |
| 229 | CH₂=CHCH₂CH₂– | H | CH₂=CHCH₂CH₂– | –NH– | CH₂=CHCH₂CH₂– | 2 |
| 230 | benzyl-CH₂– | H | CH₂=CHCH₂CH₂– | piperazine (N–N) | F₂BH | 2 |
| 231 | benzyl-CH₂– | H | CH₂=CHCH₂CH₂– | 4-methylpiperidine (N) | OCH₂CH₃ | 2 |
| 232 | benzyl-CH₂– | H | CH₂=CHCH₂CH₂– | piperazine (N–N) | CH₃ | 2 |
| 233 | benzyl-CH₂– | H | CH₂=CHCH₂CH₂– | –NH– | CH₂=CHCH₂CH₂– | 2 |
| 234 | benzyl-CH₂– | H | benzyl-CH₂– | piperazine (N–N) | F₂BH | 2 |

-continued

[Structure I: pyrrolopyrimidine scaffold with R¹, R², R³, Y, Z, m substituents]

| Compound No. | R¹ | R² | R³ | Y | Z | m |
|---|---|---|---|---|---|---|
| 235 | benzyl | H | Ac | piperazin-N-yl (N-methyl) | F₂BH | 2 |
| 236 | 4-Cl-benzyl | H | CH₂CH=CHCH₃ | −NH− | C(CH₃)=CH-CH₂CH₃ | 2 |
| 237 | 4-OCH₃-benzyl | H | CH₂CH=CHCH₃ | −NH− | C(CH₃)=CH-CH₂CH₃ | 2 |
| 238 | 3-phenylpropyl | H | CH₂CH=CHCH₃ | 4-methylpiperidin-1-yl | H | 2 |
| 239 | 3-phenylpropyl | H | CH₂CH=CHCH₃ | N-methylpiperazin-1-yl | C(=O)C(CH₃)₃ | 2 |
| 240 | 3-phenylpropyl | H | CH₂CH=CHCH₃ | −NH− | CH₂CH=CHCH₃ | 2 |

-continued

[I]

| Compound No. | R¹ | R² | R³ | Y | Z | m |
|---|---|---|---|---|---|---|
| 241 | phenyl-propyl | H | but-2-enyl | —NH— | 1-phenylethyl (CH₃) | 2 |
| 242 | phenyl-butenyl | H | pentenyl | —NH— | but-2-enyl | 2 |
| 243 | phenyl-butenyl | H | pentenyl | —N(CH₃)— | phenyl-propyl | 2 |
| 244 | Ac | H | Ac | piperazinyl | F₂BH | 2 |
| 245 | CH₃ | H | pentenyl | piperazinyl | F₂BH | 3 |
| 246 | but-2-enyl | H | pentenyl | 4-methylpiperidinyl | OAc | 3 |

-continued
[I]
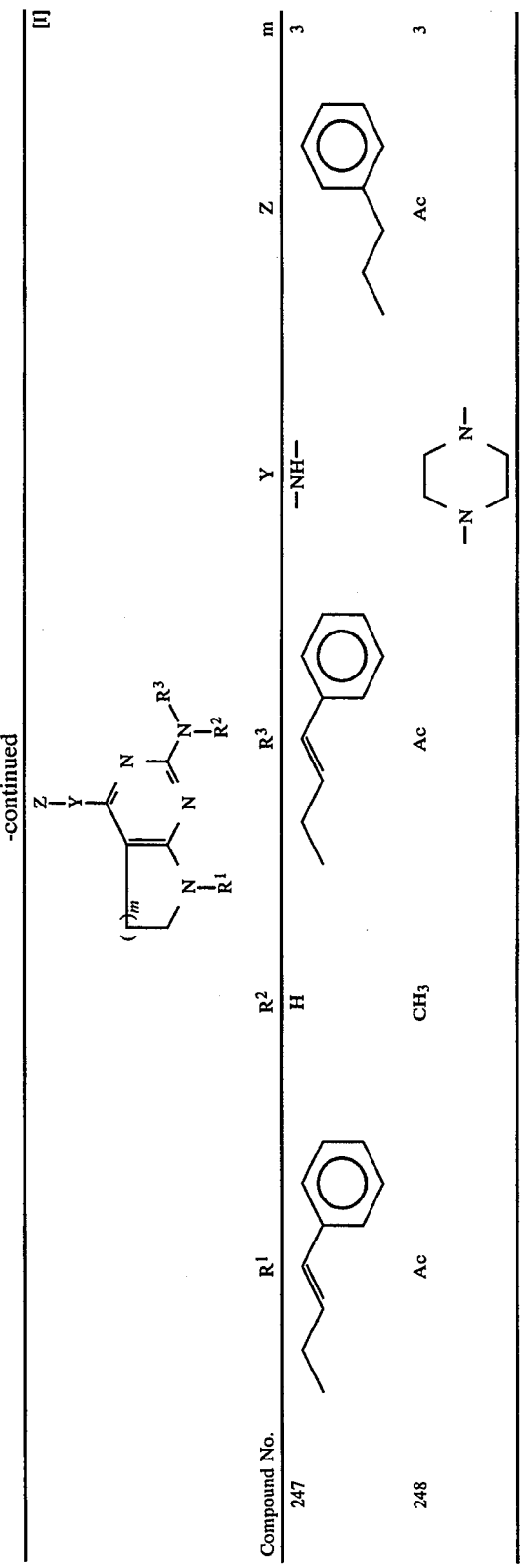
| Compound No. | R¹ | R² | R³ | Y | Z | m |
|---|---|---|---|---|---|---|
| 247 | (phenyl-CH=CH-CH₂-) | H | (phenyl-CH=CH-CH₂-) | —NH— | (phenyl-CH₂-CH₂-CH₂-) | 3 |
| 248 | Ac | CH₃ | Ac | (piperazine) | Ac | 3 | wherein F₂BH, MMTr, Ac and iPr represent

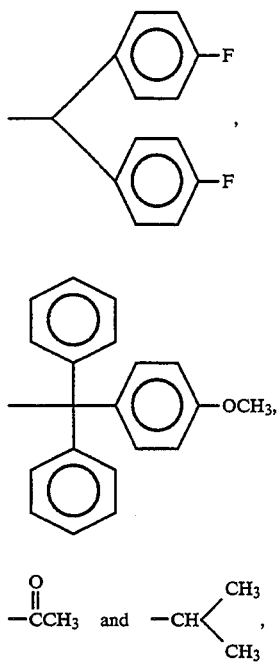

respectively.

The fused pryimidine derivatives in accordance with the present invention may be acid addition salts, and suitable examples of acids forming such salts include inorganic acids such as hydrochloric acid, hydrobromic acid, sulfuric acid, phosphoric acid, nitric acid, boric acid, carbonic acid, and the like; organic carboxylic acids such as formic acid, acetic acid, propionic acid, citric acid, succinic acid, maleic acid, oxalic acid, tartaric acid, maleic acid, fumaric acid, and the like; and organic sulfonic acids such as methanesulfonic acid, ethanesulfonic acid, benzenesulfonic acid, p-toluenesulfonic acid, camphorsulfonic acid, and the like.

According to the present invention, a fused pyrimidine derivative and pharmaceutically acceptable acid addition salt thereof can be prepared by condensation of halogenated fused pyrimidine derivative represented by the general formula [II]

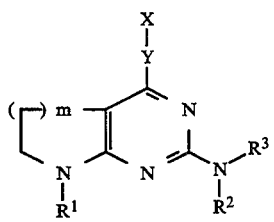

wherein $R^1$, $R^2$, $R^3$, $R^4$ and m are the same meaning as defined above and X is halogen, with a compound represented by the general formula [III]

   [III]

wherein Y and Z are the same meanings as defined above, followed by addition with an inorganic or organic acid, if necessary.

The compound of the formula [II] may be a novel or known compound. The preparation of the latter is disclosed in the art [see, R. G. Glushkov et. al., Khim. -Farm. Zh., Vol. 1, 21 (1967)]. The novel compound can be also prepared according to the reference example as described below and the above literature. Examples of the halogen atom in the halogenated fused pyrimidine derivative include a chlorine, bromine and iodine atom. Such atoms are highly reactive, and thus a desired fused pyrimidine derivative having the formula [I] can be produced by reacting such atoms with a compound represented by the formula [III].

The compound of the formula [III] adequates to this reaction may be available or prepared by a known method per se.

The compounds of the formula [III] are amines, alcohols or thiols corresponding to the groups as defined for the formula Z—Y—X. Especially the compounds corresponding to the previously listed suitable examples for the formula Z—Y— are preferable in use.

The above-described reaction can be conducted, for example, by reacting one equivalent of a halogenated fused pyrimidine derivative represented by the formula [II] with 1 to 30 equivalents of an amine, alcohol or thiol represented by the formula [III] in the absence or presence of a solvent under atomospheric pressure or into an autoclave. If necessary, the addition of a base, and examples of the base include inorganic bases such as sodium hydroxide, potassium hydroxide, sodium carbonate and potassium carbonate, and organic bases such as triethylamine, diethylaniline, dimethylaniline and pyridine.

Further, the presence of an additive may be allowed, and the additives include iodides such as potassium iodide, sodium iodide, lithium iodide, tetrabutylammonium iodide, and the like, or fluorides such as potassium fluoride, sodium fluoride, cesium fluoride, tetrabutylammonium fluoride, and the like.

The reaction temperature is in the range of −20° to 300° C., preferably in the range of room temperature to 200° C., and the reaction is completed in 72 hours.

Preferable reaction solvents include halogenated hydrocarbons such as dichloromethane, chloroform, trichloromethane and carbon tetrachloride, aromatic hydrocarbons such as benzene, toluene and xylene, alcohols such as methanol, ethanol, isopropyl alcohol, butanol and tert-butanol, ethers such as diethyl ether, tetrahydrofuran and dioxane, and aprotic polar solvents such as dimethylformamide, dimethylacetamide, dimethylsulfoxide and sulfolane, etc.

After the completion of the reaction, the reaction mixture can be subjected to ordinary separation and purification procedures, that is, concentration, solvent extraction, recrystallization, chromatography, etc., to isolate a desired fused pyrimidine derivative represented by the formula [I]. The compound [I] can be converted to a pharmaceutically acceptable acid addition salt according to a conventional method.

Also almost all the compounds of the formula [II] is novel. Newly developed synthetic routes to [I] via [II] are shown in the following scheme:

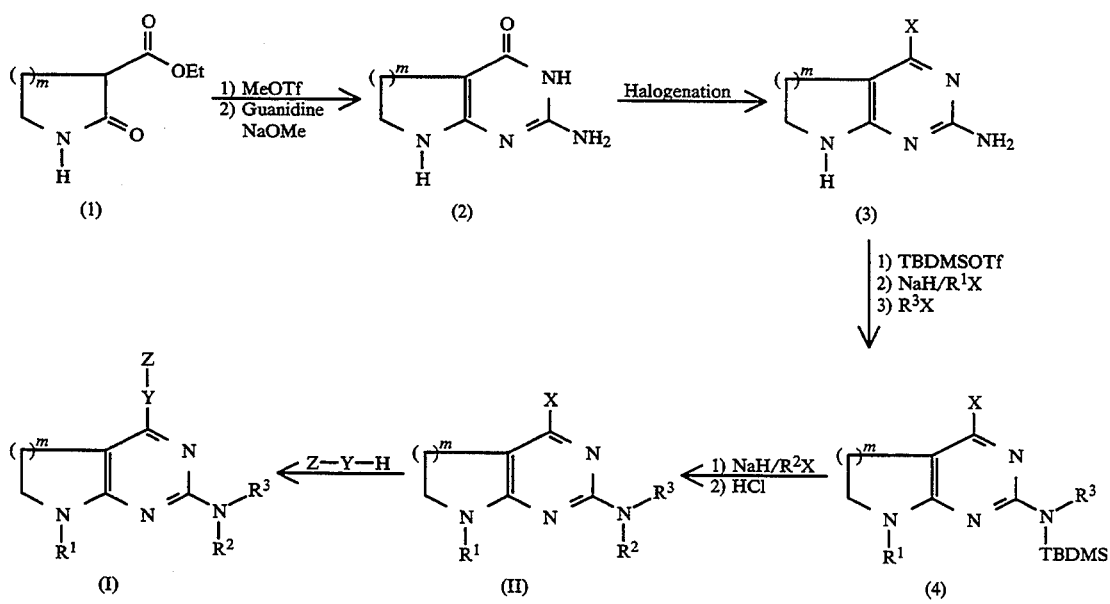

wherein, $R^1$, $R^2$ and $R^3$, and X, Y and Z have the same definitions as those of the formulae [II] and [III], and TBDMSOTf represents tert-butyldimethylsilyltrifluoromethanesulfonate.

The reaction steps up to the compound of the formula [II] are summarized, as follows:

The 3-ethoxycarbonyl alicyclic amide (1) be treated with methyl-trifluoromethanesulfonate to give an iminoether, which can be annulated with guandine in a strong alkaline condition to give the compound of the formula (2).

The resulting compound (2) can be halogenated by a general method (e.g., using phosphorus oxychloride) to give the compound of formula (3).

The compounds of the formula [I] that have a group—Y—Z via a carbon atom thereof bonded to the pyrimidine ring, are novel, and therefore a method for preparation of the same has been unknown.

Newly developed synthetic routes are shown in the following scheme:

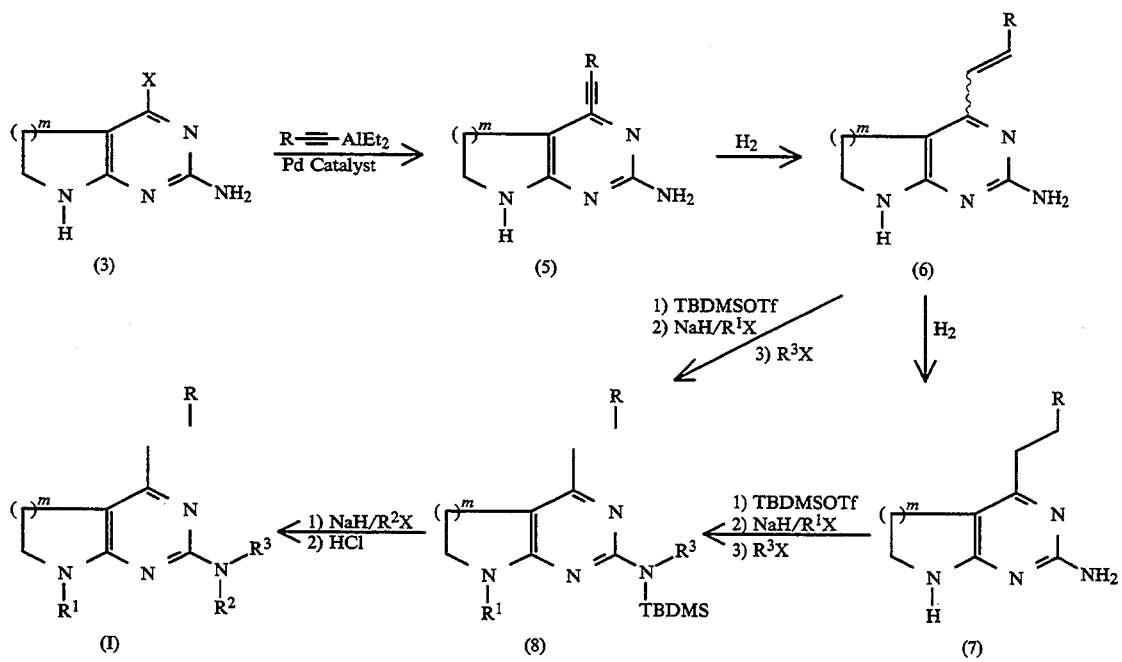

wherein $R^1$, $R^2$, and $R^3$, and X have the same definitions as those of the formula [II], and TBDMSOTf and Et represent tert-butyldimethysilyl-trifluoromethanesulfonate and an ethyl group, respectively.

The crosscoupling reaction of a compound (3) and an alkynyl metal compound, preferably diethylalkynylaluminum, can be performed in the presence of tetrakis(triphenylphosphine)palladium to afford a compound (5). Hydrogenation of (5) gives compounds (6) and (7).

Alternatively, the compounds of the formula [I] can be obtained by using a tert-butyl dimethylsilyl group as a protective group, and repeating the above to selectively introduce the substituents $R^1$, $R^2$ and $R^3$.

The present compounds exhibit an excellent pharmacological action against hypoxemia associated with various respiratory diseases.

It is generally known that, in pneumonopathy, e.g., pneumonectasis, bronchitis, bronchial asthma, interstitial pneumonia and pneumonophthisis, the partial pressure of oxygen ($PaO_2$) in arterial blood is lowered as the pathosis becomes more severe or chronic. In this case, symptoms such as a feeling of fatigue, shortness of breath and choking occur, and in a serious state, dyspnea, cyanosis and a disturbance of consciousness occur.

Therefore, a pharmaceutical preparation capable of raising and improving the $PaO_2$ lowered due to such respiratory diseases has been desired in the art. Further, it is often shown that, in such diseases, the partial pressure of carbon dioxide ($PaCO_2$) in arterial blood increases conversely to a decrease of $PaO_2$, and in this case, there is a need for a pharmaceutical preparation that cannot only increases $PaO_2$ but also decreases $PaCO_2$.

The compounds in the present invention have actions such that they enhance the respiratory function of the lung, that one mainly increases only $PaO_2$, and that another increases $PaO_2$ and decreases $PaCO_2$, at the same time, and thus the present compounds are useful for the treatment of various respiratory diseases.

The pharmacological effect of the compound in accordance with the present invention can be demonstrated by an acute hypoxemia model using an experimental animal. For example, the acute hypoxemia (having a lower $PaO_2$ value) model can be prepared by administering intratracheally a fine powder, such as carbon powder, silica gel, glass beads or dental impression material, in a small animal, e.g., rat, to lower the respiratory function [see, for example, Munakata et al., *Preprints of the 35th Symposium of Japanese Society of Anesthesiology*, 179 (1988)]. Also, acute hypoxemia (having a lower $PaO_2$ value) model can be prepared by administering intratracheally a mucosa-prophlogistic acid, e.g., acetic acid and crotonic acid.

Therefore, the compounds in the present invention were orally or parenterally administered to the above-described model animal, and the arterial blood was collected after a given period of time and subjected to a measurement of $PaO_2$ (or $PaCO_2$) by a blood gas analyzer. As a result, a significant increase of $PaO_2$ (or decrease of $PaCO_2$) in comparison with that before the administration, was observed.

The fused pyrimidine derivative and its acid addition salt in accordance with the present invention can be administered orally or as a parenteral administration such as an intravenous, subcutaneous, intramuscular, percutaneous, intrarectal or other administration.

Examples of the dosage form for the oral administration include tablets, pills, granules, powders, suspensions and capsules.

The tablets can be formulated by a conventional method through the use of, for example, excipients such as lactose, starch and crystalline cellulose; binders such as carboxymethylcellulose, methylcellulose and polyvinylpyrrolidone; and disintegrators such as sodium alginate, sodium hydrogencarbonate and sodium laurylsulfate.

Similarly, the pills, powders and granules can be formulated by a conventional method through the use of the above-described excipients, etc. The solutions and suspensions can be formulated by a conventional method through the use of, for example, glycerin esters such as tricaprylin and triacetin and alcohols such as ethanol. The capsules can be formulated by filling a granule, a powder or a solution into a capsule made of gelatin, and the like.

Examples of the dosage form for a subcutaneous, intramuscular and intravenous administration include injections in the form of an aqueous or nonaqueous solution. In the aqueous solution, use is made of, for example, a physiological saline, and the like. In the nonaqueous solution, use is made of, for example, propylene glycol, polyethylene glycol, olive oil, ethyl oleate, and the like. If necessary, preservatives, stabilizers, etc., may be added thereto. The injections can be sterilized by a proper treatment, such as a filtration through the bacterial filter, or by an addition of a bacteriocide.

Examples of the dosage forms for a percutaneous administration include ointments and creams. The ointments and creams can be formulated by a conventional method through the use of fatty oils, such as castor oil and olive oil, petrolatums, etc., in the case of the ointments, and emulsifiers, such as diethylene glycol and sorbitan monofatty acid esters, etc., in the case of the creams.

Conventional suppositories, such as gelatin soft capsules, may be used for a rectal administration.

Although the dosage of the bicyclic pyrimidine derivative of the present invention varies depending upon the kind of disease, administration path, age and sex of patient, and severity of disease, etc., it is usually 1 to 500 mg/day/adult.

All of the compounds provided by the present invention (testing substances) have more than 2 g/kg (rat, P.O.) of $LD_{50}$.

EXAMPLES

The present invention will now be described in more detail with reference to the following Examples.

Reference Example: Synthesis of 8-allyl-2-alylamino-4-chloro-5,6,7,8-tetrahydropyrido-[2,3-d]pyrimidine Procedure A A solution of 14 g (75.8 mmol) of 2-amino-4-chloro5,6,7,8-tetrahydropyrido[2,3-d]pyrimidine and 12 ml (87 mmol) of triethylamine in 240 ml of dichloromethane was cooled to 0° C., and 25.3 g (79 mmol) of p-anisylchlorodiphenylmethane was added thereto. The mixture was stirred at that temperature for one hour. The reaction mixture was poured into water and extracted twice with 200 ml of dichloromethane. The organic phase was dried over magnesium sulfate, filtered, and the solvent was evaporated to remove from the filtrate. To a solution of 36.2 g of the resultant crude product in 150 ml of DMF was added. 15.3 ml (167 mmol) of allyl iodide, the mixture was cooled to 0° C., and treated with 10 g (250 mmol) of sodium hydride (oleaginous, 60%). It was stirred at that temperature for 2 hours. The reaction mixture was gradually dropwise poured onto iced water, acidified with 80 ml of 5N hydrochloric acid, heated at 70° C. and stirred for 2 hours. The byproduct and decomposed material were extracted twice with 200 ml of an ether/hexane (=1/1) solution from the reaction mixture. The water layer was neutralized with 5N sodium hydroxide and the product was extracted with ethyl acetate. The organic layer was dried over magnesium sulfate and filtered, and the solvent was evaporated to be removed from the filtrate. Recrystallization from hexane-isopropyl ether yield 6.71 g (33%) of the desired 8-allyl-2-allylamino-4-chloro-5,6,7,8-tetrahydropyrido[2,3-d]pyrimidine.

Procedure B

To a solution of 69 g (370 nmol) of 2-amino-4-chloro-5,6,7,8-tetrahydropyrido[2,3-d]pyrimidine in anhydrous dichloromethan (450 ml) was added 70 ml (500 mmol) of triethylamine, and then cooled to −37° C. Then, under inert gas atmosphere, to the reaction mixture was dropwise added 102 ml (450 mmol) of tertbutyldimethylsilyl trifluoromethanesulfonate over a period of 30 minutes, and the mixture was stirred at that temperature for 1.5 hours. The suspension turned to a red-colored solution. The reaction solution was poured into 300 ml of water. After usual work up, the product was extracted with 300 ml of dichloromethane. The combined dichloromethane layer was dried over potassium carbonate, and then the solvent was evaporated from the filtrate. To the resulting oily residue was added 300 ml of hexane, then heated to 80° C. with stirring. An insoluble oily residue then removed by decantation. The target compound was extracted with 200 ml of hexane from the oily residue. The combined hexane layer was evaporated to give 112 g (370 mmol) of 2-tert-butyl-dimethylsilylamino-4-chloro-5,6,7,8tetrahydropyrido[2,3-d]pyrimidine in the form of white crystals. (Yield 99%)

Physical Properties $^1$H-NMR(CDCl$_3$)$\sigma$:

0.23 (6H, s), 0.93 (9H, s), 1.89 (2H, tt, J=6 and 6 Hz), 2.61 (2H, t, J=6 Hz), 3.33 (2H, dt, J=2.5 and 6 Hz), 4.3 (1H, br), 5.0 (1H, br)

125 g (420 mmol) of 2-tert-butyldimethylamino-4-chloro-5,6,7,8-tetrahydropyrido[2,3-d]pyrimidine thus obtained and 87 ml (1.00 mol) of allylbromide were dissolved in 630 ml of anhydrous DMF, and the solution was cooled to 0° C. Then, under inert gas atmosphere, to the solution was slowly added a suspension of 60% sodium hydride 42 g (1.00 mol) in DMF (150 ml), followed by a further stirring for one hour at room temperature. After the reaction was completed, it was treated with 1 l of cooled water, and extracted with hexane (500 ml ×2). The combined organic layer was dried over sodium sulfate, and concentrated to yield oily residue. Then, to it residue was added 150 ml of 12N hydrochloric acid and 200 ml of water, followed by stirring for 15 minutes. The impurities were extracted with hexane (250 ml ×2). To the water layer was added ammonia water until the formation of the precipitation was completed. The resulting precipitates were filtered off, washed with water, dried, and 95 g of crude products thus obtained were recrystallized from 400 ml of ethanol to yield 83 g (315 mmol) of the title compound. (Yield 75%)

Physical Properties:

$^1$H-NMR(CDCl$_3$)$\sigma$:

1.87 (2H, tt, J=5.5 and 6 Hz), 2.63 (2H, t, J=6 Hz), 3.28 (2H, t, J=5.5 Hz), 3.96 (2H, t, J=5.5 Hz), 4.8 (1H, br), 5.0–5.2 (4H, m), 5.5–6.1 (2H, m)

UV (EtOH) λmax, nm 300, 223 m.p. 107.5°–108.0° C.

Example 1: Synthesis of 8-allyl-2-allylamino-4-(4-methyl-1-piperazinyl)-5,6,7,8-tetrahydropyrido[2,3-d]pyrimidine A mixture of 43 g (160 mmol) of 8-allyl-2-allylamino-4-chloro-5,6,7,8-tetrahydropyrido[2,3-d]pyrimidine prepared in Reference Example A or B, 22 g (170 mmol) of lithium iodide, and 300 ml of N-methylpiperazine in an autoclave was stirred at 160° C. for 15 hours. After the reaction was completed, the reaction solution was washed with 1 l of water, and extracted with ethylacetate (500 ml ×4). The resulting organic layer was washed with water (500 ml ×3), dried over sodium sulfate, filtered, and then concentrated to give 50 g of oily residue. The resulting oily residue was recrystallized from 500 ml of hexane to yield 40 g of 8-allyl-2-allylamino-4-(4-methyl-1-piperazinyl)-5,6,7,8-tetrahydropyrido[2,3-d]pyrimidine. (prisms; mp. 81° C.) To the mixture was added 170 ml of acetonitrile, dissolved at 70° C., and then cooled to −15° C., followed by recrystallization to yield 37.8 g (yield 69%) of a free base. (needles; mp. 80.5°–81.5° C.). Then, 70.0 g of the free base derived from the same procedure was ground in a mortar, dissolved in 600 ml of diethylether. To the solution was added saturated hydrogen chloride ether solution with stirring until precipitation was completed. The precipitate was filtered and thoroughly washed with diethylether to yield 84.6 g of the hydrochloride in the form of white crystals. The crude crystals were recrystallized from 550 ml of isoprapanol to yield 74 g of 8-allyl-2-allylamino-4-(4-methyl-1-piperazinyl)-5,6,7,8-tetrahydropyrido[2,3-d]pyrimidine hydrochloride. (yield of the hydrochloride 87%)

Physical Properties of Free Base:

$^1$H-NMR(CDCl$_3$)$\sigma$:

1.7–1.9 (2H,m), 2.37 (3H, s), 2.47 (2H, t, J=6 Hz), 2.58 (4H, t, J=4.5 Hz), 3.29 (2H, t, J=5.5 Hz), 3.36 (4H , t, J=4.5 Hz), 3.96 (2H, t, J=5 Hz), 4.20 (2H, d, J=6 Hz), 4.5 (1H, br), 5.0–5.3 (4H, m), 5.6–6.1 (2H, m)

Physical Properties of Hydrochloride:

UV (EtOH) λmax, nm 224, 302

Elemental Analysis: for $C_{18}H_{31}N_6Cl_2$

Calculated: C. 53.86: H. 7.54: N. 20.93: $C_{1.17.66}$

Found: C. 53.79: H. 7.46: N. 20.81: $C_{1.17.56}$

Example 2: Synthesis of 2-N,N-diallylamino-4-(2-Phenylethyl)-5,6,7,8-tetrahydropyrido [2,3-d]pyrimidine Under argon atmosphere, to a solution (380 μl, 3.5 mmol) of phenylacetylene in anhydrous tetrahydrofuran (THF) was added a 1.58M solution (2.0 ml, 3.3 mmol) of butyllithium in hexane at 0° C. and stirred at the same temperature for 15 minutes, and to the reaction mixture was further added a 1M solution (3.3 ml, 3.3 mmol) of diethylaluminium chloride in hexane, and stirred at room temperature for 15 minutes. Then, to the reaction solution was added tetrakis (triphenylphosphine) palladium (120 mg, 0.1 mmol) and 2-amino-4-chloro-5,6,7,8-tetrahydropyrido[2,3-d]pyrimidine (185 mg, 1 mmol), which was stirred at reflux temperature for 7 hours. The reaction solution was treated with an aqueous sodium hydroxide solution and extracted with ethylacetate. Then, the organic layer was dried, and concentrated. The resulting residue was purified with alumina column chromatography (mobile phase: ethylacetate/hexane=2/1) to yield 63 mg (0.25 mmol, 25%) of 2-amino-4-phenylethynyl-5,6,7,8-tetrahydropyrido[2,3-d]pyrimidineo
Physical Properties
¹H-NMR(CDCl₃)σ:
1.95 (2H, m), 2.80 (2H, t, J=6 Hz), 3.3–3.5 (2H, m), 4.7 (2H, br), 5.5 (1H, br), 7.2–7.6 (5H, m)
IR (KBr) 1570, 1600, 2200, 3100, 3250 cm⁻¹

To a solution of the resulting 2-amino-4-phenylethynyl-5,6,7,8-tetrahydropyrido[2,3-d]pyrimidine-(1.9 g, 7.5 mmol) in 15 ml ethanol-acetic acid (8:1) was added 300 mg platinum oxide. The mixture was stirred in an atmosphere of hydrogen at room temperature for 4 hours. After the reaction was completed, the solution was filtered, the filtrate was neutralized, and extracted with dichloromethane, and the organic layer was dried and concentrated to yield a residue. The residue was purified with ODS partition chromatography (mobile phase: methanol) to yield 1.2 g of a mixture containing 2-amino-4-(2-phenylethyl)-5,6,7,8-tetrahydropyrido[2,3-d]pyrimidine as a main component.
Physical Properties:
¹H-NMR(CDCl₃)σ:
1.8–2.0 (2H, m), 2.3–2.9 (4H, m), 2.6 (2H, t, J=6 Hz), 3.2–3.4 (2H m), 4.7 (2H, br), 5.3 (1H, br), 7.2–7.3 (5H, m)

A solution of the resulting 2-amino-4-(2-phenylethyl)-5,6,7,8-tetrahydropyrido[2,3-d]pyrimidine (120 mg, 0.54 mmol) and allyliodide (440 μl, 4.8 mmol) in 1.5 ml of anhydrous DMF was cooled to 0° C., sodium hydride (60%, 210 mg, 5.4 mmol) was added under nitrogen or argon atmosphere, and the mixture was stirred at room temperature for 3 hours. After the reaction was completed, the reaction solution was washed with water, extracted, dried and concentrated. The resulting residue was purified with silica-gel column chromatography (mobile phase: ethylacetate/hexane=1/1 to 2/1) to yield 40 mg (0.11 mmol) (yield 20%) of 2-N,N-diallylamino-4-(2-phenylethyl)-5,6,7,8-tetrahydropyrido[2,3-d]pyrimidine.
Physical Properties:
¹H-NMR(CDCl₃)σ:
1.7–1.9 (2H, m), 2.44 (2H, t, J=6 Hz) 2.6–2.8 (2H, m), 2.9–3.1 (2H, m) 3.21 (2H, t, J=5.5 Hz), 4.09 (6H, d, J=5.5 Hz), 5.0–5.2 (6H, m), 5.6–6.1 (3H, m), 7.21 (5H, s)

In the following Examples, the compounds in accordance with the present invention were prepared by the procedures described in Example 1 or 2, using corresponding starting materials and reactants, respectively, as well as reaction solvents, coexisting bases and additives indicated in the following tables, and each reaction was performed under the conditions, i.e., reaction temperature, reaction time, and reaction vessel, indicated in the following tables.

(*A: Autoclave B: Atmospheric pressure)

| Ex. No. | Compound No. | ¹H-NMR data of free base (CDCl₃) δ(ppm) | Yield of free base (%) | Type of salt M.P. of acid addition salt Recrystallization solvent | UV of acid addition salt EtOH $\lambda_{max}$ (nm) | Reaction solvent Coexisting base Additive | Reaction temp. Reaction time Reaction vessel |
|---|---|---|---|---|---|---|---|
| 3 | 104 | 3.06(6H, s), 2.8–3.45(4H, m), 3.8–4.1(4H, m), 4.5(1H, br), 4.9–5.3(4H, m), 5.4–6.2(2H, m) | 28 | HCl.salt 102° C. EtOH/Et₂O | — | DMF — LiI | 160° C. 44 h A |
| 4 | 107 | 1.7–1.9(2H, br), 2.3–2.5(6H, m, br), 2.85(3H, d, J=5Hz), 3.2(6H, t-like), 4.25(1H, s), 4.4(1H, br), 4.8(1H, br), 6.96(4H, t, J=9Hz), 7.25–7.45(4H, m) | 72 | — | — | — — LiI | 170° C. 20 h B |
| 5 | 108 | 1.7–1.8(2H, m, br), 2.4(2H, t-like), 2.41(4H, t-like), 3.2(6H, br), 3.94(2H, t, J=5.5Hz), 4.24(1H, s), 4.5(1H, t, J=5.5Hz), 4.8(1H, br), 5.0(1H, dd, J=9&2Hz), 5.18(1H, dd, J=14&2Hz), 5.7–6.1(1H, m), 6.96(4H, t, J=9Hz), 7.25–7.45(4H, m) | 65 | HCl.salt | 206 245 306 | DMF — | 170° C. 16 h B |
| 6 | 112 | 1.7–1.9(2H, br), 1.73(3H, s), 2.4(2H, br), 2.41(4H, br), 3.26(4H, br), 3.3(2H, br), 3.87(2H, d, J=6Hz), 4.24(1H, s), 4.6(1H, t, J=6Hz), 4.77(1H, br), 4.8(1H, br), 4.85 (1H, br), 6.96(4H, t, J=9Hz), 7.2–7.4(4H, m) | 55 | HCl.salt | 206 245 306 | — — LiI | 170° C. 20 h B |
| 7 | 117 | 1.6–1.9(2H, br), 2.3–2.5(6H, m), 2.89(3H, d, J=5Hz), 3.08(3H, s), 3.19(4H, t, J=5Hz), 3.20(2H, t, J=5Hz), 4.24(1H, s), 4.5(1H, br), 6.95(4H, t, J=8.5Hz), 7.25–7.43(4H, m) | 75 | HCl.salt | — | — — LiI | 170° C. 15 h B |
| 8 | 120 | 1.6–1.9(2H, br), 2.40(2H, t-like), 2.42(4H, t-like), 3.06(3H, s), 3.18(4H, t-like), 3.20(2H, br), 3.97(2H, t, J=5.5Hz), 4.24(1H, s), 4.5(1H, t, br, J=6Hz), 5.05 (1H, dd, J=8&1Hz), 5.2(1H, dd, J=15&1Hz), 5.7–6.2(1H, m), 6.96(4H, t, J=9Hz), 7.25–7.43(4H, m) | 58 | HCl.salt 152~156° C. — | — | — — LiI | 170° C. 20 h B |
| 9 | 121 | 1.7–2.1(2H, m), 2.29(2H, t-like, J=6.4Hz), 3.03(3H, s), 3.21(2H, dd, J=3.7Hz, 5.5Hz), 3.8–4.2(5H, m), 4.5(1H, br), 4.9–5.4(4H, m), 5.8–6.2(2H, m) | 100 | HCl.salt 123~125° C. acetone | 298 234 | — — LiI | 170° C. 15 h A |
| 10 | 129 | 1.6–1.9(2H, m, br), 2.4–2.5(6H, m, br), 2.54(3H, s), 3.07(3H, s), 3.21(4H, t, J=5Hz), 3.31(2H, t-like), 4.25(1H, s), 6.97(4H, t, J=9Hz), 7.25–7.45(4H, m) | 25 | — | — | DMF — — | 120° C. 10 h B |
| 11 | 130 | 0.87(3H, t, J=7Hz), 1.5–1.9(4H, m), 2.41(2H, t, J=5.5Hz), 2.42(4H, br), 3.16(4H, t, J=5Hz), 3.25(2H, m), 3.46(2H, t, J=7Hz), 3.95(2H, t, J=5.5Hz), 4.24 (1H, s), 4.5(1H, t-like), 5.05(1H, dd, J=9&2Hz), 5.7–6.2(1H, m), 5.2(1H, dd, J=15&2Hz), 6.96(4H, t, J=9Hz), 7.25–7.43(4H, m) | 75 | HCl.salt 159~164° C. | 205 220 308 | — — LiI | 170° C. 20 h B |
| 12 | 131 | 0.87(3H, t, J=7.5Hz), 1.55(2H, m), 1.8(2H, m, br), 2.4(6H, t-like, br), 2.54(3H, s), 3.21(4H, t, J=5Hz), 3.31(2H, t, J=5Hz), 3.45(2H, t, J=7.5Hz), 4.25(1H, s), 6.96(4H, t, J=9Hz), 7.25–7.45(4H, m) | 30 | — | — | DMF — — | 120° C. 15 h B |

-continued

| Ex. No. | Compound No. | ¹H-NMR data of free base (CDCl₃) δ(ppm) | Yield of free base (%) | Type of salt M.P. of acid addition salt Recrystallization solvent | UV of acid addition salt EtOH $\lambda_{max}$ (nm) | Reaction solvent Coexisting base Additive | (*A: Autoclave B: Atmospheric pressure) Reaction temp. Reaction time Reaction vessel |
|---|---|---|---|---|---|---|---|
| 13 | 134 | 0.2–0.5(4H, m), 0.9(1H, m), 1.7–1.9(2H, m), 2.40(2H, t, J=5Hz), 2.42(4H, t, J=5Hz), 3.17(4H, t, J=5Hz), 3.36(2H, t, J=5Hz), 3.44(2H, d, J=7Hz), 3.95(2H, t, J=5.5Hz), 4.24(1H, s), 4.5(1H, t, J=6Hz), 5.05(1H, dd, J=9&2Hz), 5.2(1H, dd, J=14&2Hz), 6.96(4H, t, J=9Hz), 7.25–7.45(4H, m) | 65 | HCl.salt 133~135° C. — | — | — LiI | 170° C. 20 h B |
| 14 | 140 | 0.2–0.5(4H, m), 0.8–1.3(1H, m), 1.7–1.9(2H, br), 2.4–2.5(6H, br), 2.54(3H, s), 3.21(4H, t, J=5Hz), 3.39(2H, t, J=5Hz), 3.42(2H, d, J=7Hz), 4.25(1H, s), 6.97(4H, t, J=9Hz), 7.25–7.45(4H, m) | 20 | — | — | DMF — — | 120° C. 10 h B |
| 15 | 143 | 1.81(4H, m), 1.7–1.9(2H, m), 2.59(2H, t, J=5.5Hz), 3.20(2H, t, J=5.5Hz), 3.48(4H, t, J=6.5Hz), 3.94(2H, t, J=5.5Hz), 4.18(2H, d, J=5.5Hz), 4.5(1H, br), 5.0–5.3(4H, m), 5.6–6.2(2H, m) | 87 | HCl.salt 95~98° C. iPr₂O-iPrOH | 207 241 307 | — — LiI | 140° C. 15 h A |
| 16 | 145 | 1.59(2H, br), 1.61(4H, br), 1.7–1.9(2H, m), 2.48(2H, t, J=6Hz), 3.10(4H, t-like, br), 3.25(2H, t, J=5.5Hz), 3.96(2H, t, J=6Hz), 4.18(2H, d, J=6Hz), 4.50(1H, br), 5.0–5.3(4H, m), 5.6–6.2(2H, m) | 80 | HCl.salt 94~95° C. iPr₂O-iPrOH | 218 240 308 | — — LiI | 150° C. 15 h A |
| 17 | 146 | 1.7–2.0(6H, m, br), 2.5(2H, t, J=6Hz), 2.6–3.0(4H, m), 3.3(2H, t, J=5.5Hz), 3.6(1H, br), 3.8(1H, br), 4.0(2H, t, J=6Hz), 4.2(2H, d, J=6Hz), 4.5(1H, br), 5.0–5.3(4H, m), 5.6–6.1(2H, m), 7.3(5H, s) | 83 | fumarate 154.5~159.5° C. EtOH | 213 300 | — — LiI | 150° C. 30 h A |
| 18 | 147 | 1.5–2.1(6H, m, br), 2.47(2H, t, J=5Hz), 2.6(1H, br), 2.7–3.0(2H, m), 3.25(2H, t, J=5Hz), 3.4–3.7(3H, m), 3.94(2H, t, J=5.5Hz), 4.17(2H, d, J=5.5Hz), 4.7(1H, br), 5.0–5.3(4H, m), 5.6–6.1(2H, m) | 47 | — | — | — — LiI | 130° C. 20 h B |
| 19 | 148 | 1.6–1.9(6H, m, br), 2.05(3H, s), 2.47(2H, t, J=5.5Hz), 2.8–3.4(4H, m, br), 3.29(2H, t, J=5Hz), 3.5(1H, t-like), 3.96(2H, t, J=5.5Hz), 4.18(2H, d, J=5.5Hz), 4.5(1H, br), 5.0–5.3(4H, m), 5.6–6.1(2H, m) | 25 | fumarate 144~147° C. EtOH | 218 298 | DMF — — | 120° C. 10 h B |
| 20 | 153 | 1.5–1.9(9H, m, br), 1.8–2.0(2H, m, br), 2.51(2H, t, J=6Hz), 3.21(2H, t, J=6Hz), 3.45(4H, t, J=5.5Hz), 3.95(2H, t, J=5.5Hz), 4.18(2H, d, J=5.5Hz), 4.4(1H, br), 5.0–5.3(4H, m), 5.6–6.1(2H, m) | 75 | HCl.salt | 215 243 310 | — — LiI | 150° C. 15 h A |
| 21 | 154 | 1.7–2.0(2H, m), 2.48(2H, t, J=6Hz), 2.9–3.0(4H, m), 3.0–3.1(4H, m), 3.26(2H, t, J=5.5Hz), 3.96(2H, t, J=5.5Hz), 4.18(2H, d, J=5.5Hz), 4.6(1H, br), 5.0–5.3(4H, m), 5.6–6.1(2H, m) | 85 | fumarate | — | — — LiI | 140° C. 15 h A |
| 22 | 156 | 1.10(3H, t, J=7.3Hz), 1.6–1.9(2H, m), 2.3–2.6(8H, m), 3.1–3.3(6H, m), 3.95(2H, t-like, J=5.5Hz), 4.18(2H, d-like, J=5.5Hz), 4.55(1H, br-t, J=5.5Hz), 4.9–5.3(4H, m), 5.6–6.2(2H, m) | 100 | HCl.salt 200~210° C. i-PrOH-i-Pr₂O | 302 223 | — — LiI | 160° C. 15 h A |
| 23 | 157 | 1.7–1.9(2H, m), 2.52(2H, t, J=6Hz), 3.0–3.4(10H, m), 3.97(2H, t, J=5.5Hz), 4.19(2H, d, J=5.5Hz), 4.6(1H, br), 5.0–5.3(4H, m), 5.6–6.1(2H, m), 6.8–7.1(4H, m) | 65 | HCl.salt 168~170° C. | 206 243 307 | — — LiI | 160° C. 15 h B |
| 24 | 158 | 1.7–1.9(2H, m), 2.4–2.6(6H, m), 3.19(4H, t, J=5Hz), 3.24(2H, t, J=5Hz), 3.49(2H, s), 3.95(2H, t, J=5.5Hz), 4.18(2H, t, J=5.5Hz), 4.6(1H, br), 5.0–5.3(4H, m), 5.6–6.1(2H, m), 6.98(2H, t, J=9Hz), 7.2–7.3(2H, m) | 70 | HCl.salt | 211 242 307 | — — LiI | 160° C. 15 h B |
| 25 | 159 | 1.7–1.9(2H, m), 2.4(6H, m, br), 3.18(4H, t, J=5Hz), 3.23(2H, t, J=5.5Hz), 3.95(2H, t, J=5.5Hz), 4.17(2H, d, J=6Hz), 4.24(1H, s), 4.5(1H, t, J=5.5Hz), 5.0–5.3(4H, m), 5.7–6.1(2H, m), 6.96(2H, t, J=9Hz), 7.3–7.45(4H, m) | 40 | HCl.salt 131~133° C. iPrOH | 205 243 309 | — — LiI | 140° C. 12 h A |
| 26 | 163 | 1.5–2.15(4H, m), 2.36(3H, s), 2.3–2.75(6H, m), 3.1–3.3(2H, m), 3.4–3.6(4H, m), 3.94(2H, t-like, J=5.5Hz), 4.18(2H, d-like, J=5.5Hz), 4.5(2H, br-t, J=5.5Hz), 4.95–5.35(4H, m), 5.6–6.2(2H, m) | 96 | HCl.salt 140~142° C. i-PrOH-i-Pr₂O | 307 223 | — — LiI | 160° C. 15 h A |
| 27 | 164 | 1.7–2.1(2H, m), 2.35(2H, t-like, J=6.4Hz), 3.23(2H, t-like, J=6.1Hz), 3.8–4.6(7H, m), 4.9–5.3(4H, m), 5.5–6.2(2H, m) | 68 | HCl.salt 183~188° C. EtOH-Et₂O | 292 238 | H₂O — — | 195° C. 7 h A |
| 28 | 165 | 1.7(1H, br), 1.7–1.9(2H, m), 2.27(2H, t, J=6Hz), 2.95(3H, d, J=5Hz), 3.19(2H, t, J=5.5Hz), 3.99(2H, t, J=5.5Hz), 4.16(2H, d, J=5.5Hz), 4.5(1H, br), 5.0–5.3(4H, m), 5.7–6.1(2H, m) | 41 | fumarate 155~158° C. EtOH | 210 291 | CH₃NHCHO K₂CO₃ — | 160° C. 50 h A |
| 29 | 166 | 1.7(1H, br), 1.7–1.9(2H, m), 2.29(2H, t, J=6Hz), 3.19(2H, t, J=5.5Hz), 3.36(3H, s), 3.50–3.65(4H, m), 3.96(2H, t, J=5.5Hz), 4.16(2H, d, J=5.5Hz), 4.4(1H, br), 5.0–5.3(4H, m), 5.7–6.1(2H, m) | 59 | fumarate 151.5~152.5° C. EtOH | 211 291 | — — LiI | 180° C. 15 h A |
| 30 | 168 | 1.6(1H, br), 1.7–1.9(2H, m), 2.29(2H, t, J=6Hz), 3.19(2H, t, J=5.5Hz), 3.96(2H, t-like, J=5.5Hz), 4.03(2H, t, J=5.5Hz), 4.16(2H, d, J=5.5Hz), 4.5(1H, br), 5.0–5.3(6H, m), 5.7–6.1(3H, m) | 53 | fumarate 149~150.5° C. EtOH | 212 291 | — — LiI | 180° C. 15 h A |

| Ex. No. | Compound No. | $^1$H-NMR data of free base (CDCl$_3$) δ(ppm) | Yield of free base (%) | Type of salt M.P. of acid addition salt Recrystallization solvent | UV of acid addition salt EtOH $\lambda_{max}$ (nm) | Reaction solvent Coexisting base Additive | Reaction temp. Reaction time Reaction vessel (*A: Autoclave B: Atmospheric pressure) |
|---|---|---|---|---|---|---|---|
| 31 | 169 | 1.75–2.15(2H, m), 2.43(2H, t-like, J=6.5Hz), 3.25(2H, t-like, J=5Hz), 3.85–4.05(2H, m), 4.1–4.3(2H, m), 4.6–4.9(1H, br), 4.95–5.35(4H, m), 5.6–6.2(3H, m), 6.9–7.6(5H, m) | 30 | fumarate 147~150° C. EtOH | — | — LiI | 190° C. 5 h B |
| 32 | 170 | 1.8–2.05(2H, m), 2.1–2.4(2H, m), 3.20(2H, t-like, J=5.3Hz), 3.97(2H, t-like, J=5.3Hz), 4.1–4.7(6H, m), 4.9–5.3(4H, m), 5.6–6.2(2H, m), 7.2–7.5(5H, m) | 65 | HCl.salt 142~143° C. i-PrOH | 299 237 208 | — LiI | 160° C. 14 h B |
| 33 | 171 | 1.7–1.9(2H, m), 2.14(2H, t, J=6Hz), 2.86(2H, t, J=7Hz), 3.17(2H, t, J=5.5Hz), 3.65(2H, q, J=6.5Hz), 4.00(2H, t, J=5.5Hz), 4.15(2H, d, J=5.5Hz), 4.5(1H, br), 5.0–5.3(4H, m), 5.7–6.1(2H, m) | 81 | fumarate 154~158° C. EtOH | 210 289 | — LiI | 150° C. 40 h A |
| 34 | 172 | 1.8–2.2(4H, m), 2.84(2H, t, J=7.0Hz), 3.18(2H, t-like, J=5.3Hz), 3.6(2H, q-like, J=6.4Hz), 3.8–4.2(5H, m), 4.5(1H, br), 4.9–5.3(4H, m), 5.55–6.2(2H, m), 7.0–7.3(4H, m) | 68 | fumarate 105~109° C. EtOH | 288 225 | — LiI | 170° C. 17 h B |
| 35 | 173 | 1.7–2.3(4H, m), 2.80(2H, t, J=6.4Hz), 3.17(2H, t-like, J=5.5Hz), 3.7(2H, q-like, J=6.1Hz), 3.79(3H, s), 3.7–4.2(5H, m), 4.5(1H, br-t), 4.9–5.3(4H, m), 5.6–6.2(2H, m), 6.88(2H, d, J=9.3Hz), 7.12(2H, d, J=9.3Hz) | 59 | fumarate 91~93° C. EtOH | 287 226 | — LiI | 170° C. 6 h B |
| 36 | 175 | 2.16(2H, t, J=6Hz), 2.67(2H, t, J=7.5Hz), 3.15(2H, t-like, J=5.5Hz), 3.42(2H, dt, J=7&6Hz), 3.94(2H, t, J=5.5Hz), 4.13(2H, d, J=5.5Hz), 4.5(1H, br, t-like), 5.0–5.3(4H, m), 5.6–6.1(2H, m), 7.19(5H, s) | 97 | fumarate 141~144° C. EtOH | 292 215 | — LiI | 140° C. 20 h A |
| 37 | 176 | 1.6–2.2(12H, m), 3.12(2H, t-like, J=6.2Hz), 3.5–3.8(3H, m), 3.97(2H, t-like, J=5.9Hz), 4.18(2H, d-like, J=5.9Hz), 4.45(1H, br-t, J=5.5Hz), 4.95–5.3(4H, m), 5.6–6.2(2H, m), 7.2–7.4(5H, m) | 60 | — — — | — | — LiI | 180° C. 5 h B |
| 38 | 177 | 1.6–2.3(10H, m), 3.13(2H, t-like, J=4.2Hz), 3.5–3.8(3H, m), 3.97(2H, t-like, J=6Hz), 4.13(2H, d-like, J=6Hz), 4.5(1H, br-t, J=6Hz), 5.0–5.4(4H, m), 5.6–6.2(2H, m), 6.9–7.4(4H, m) | 81 | fumarate 136~140° C. EtOH | 289 213 | — LiI | 180° C. 4 h B |
| 39 | 178 | 1.6–2.1(4H, m), 3.12(2H, t-like, J=4.3Hz), 3.8–4.6(8H, m), 4.9–5.3(4H, m), 5.6–6.2(2H, m), 7.1–7.4(10H, m) | 47 | fumarate 110~120° C. EtOH | 290 213 | — LiI | 180° C. 8 h B |
| 40 | 183 | 1.6–2.2(2H, m), 2.50(2H, t, J=6.4Hz), 3.31(2H, t-like, J=3.5Hz), 3.90(2H, t-like, J=4.1Hz), 4.20(2H, d-like, J=5.7Hz), 4.6–5.3(6H, m), 5.6–6.1(2H, m), 7.2–7.6(3H, m), 7.7–8.0(2H, m) | 13 | fumarate 119~120° C. EtOH | 311 221 | DMF — | 150° C. 20 h B |
| 41 | 184 | 1.7–1.9(2H, m), 2.53(2H, t, J=6Hz), 2.83(6H, s), 3.25(2H, t, J=5.5Hz), 3.97(2H, t, J=5.5Hz), 4.19(2H, d, J=5.5Hz), 4.5(1H, br), 5.0–5.3(4H, m), 5.6–6.1(2H, m) | 63 | HCl.salt 127~129° C. iPr$_2$O | 214 243 307 | DMF K$_2$CO$_3$ — | 150° C. 40 h A |
| 42 | 185 | 1.13(3H, t, J=7Hz), 1.7–1.9(2H, m), 2.50(2H, t, J=6Hz), 2.80(3H, s), 3.18(2H, t, J=7Hz), 3.22(2H, t, J=5.5Hz), 3.96(2H, t, J=5.5Hz), 4.19(2H, d, J=5.5Hz), 4.5(1H, br), 5.0–5.3(4H, m), 5.6–6.1(2H, m) | 65 | HCl.salt 103~105° C. iPr$_2$O-iPrOH | — | — LiI | 150° C. 30 h A |
| 43 | 186 | 1.6(1H, br), 1.7–1.9(2H, m), 2.54(2H, t, J=6Hz), 2.93(3H, s), 3.26(2H, t, J=5.5Hz), 3.47(2H, t-like, J=5Hz), 3.7–3.9(2H, m), 3.92(2H, t, J=5.5Hz), 4.18(2H, d, J=5.5Hz), 4.6(1H, br), 5.0–5.3(4H, m), 5.6–6.1(2H, m) | 61 | HCl.salt 73–73.5° C. iPr$_2$O-CH$_3$CO$_3$Et | 217 242 307 | — LiI | 160° C. 15 h A |
| 44 | 187 | 0.91(3H, t, J=6.5Hz), 1.0–1.7(4H, m), 1.7–1.9(2H, m), 2.50(2H, t, J=6Hz), 2.81(3H, s), 3.22(2H, t, J=6.5Hz), 3.24(2H, t, J=5.5Hz), 3.96(2H, t, J=5.5Hz), 4.19(2H, d, J=5.5Hz), 4.5(1H, br), 5.0–5.3(4H, m), 5.6–6.1(2H, m) | 63 | HCl.salt 74~76.5° C. iPrOH | 217 241 307 | — LiI | 150° C. 80 h A |
| 45 | 189 | 1.7–1.9(2H, m), 2.56(2H, t, J=6Hz), 2.75(3H, s), 3.25(2H, t, J=5.5Hz), 3.96(2H, t, J=5.5Hz), 4.20(2H, d, J=5.5Hz), 4.42(2H, s), 4.5(1H, br), 5.0–5.4(4H, m), 6–6.1(2H, m), 7.30(5H, s-like) | 40 | fumarate 102~102.5° C. EtOH | 213 298 | — LiI | 150° C. 30 h A |
| 46 | 192 | 1.6–1.9(2H, m), 2.46(2H, t-like, J=5.3Hz), 2.7–3.0(2H, m), 2.86(3H, s), 3.1–3.5(4H, m), 3.97(2H, t, J=5.5Hz), 4.18(2H, d-like, J=5.5Hz), 4.5(1H, br-t, J=5.5Hz), 4.9–5.3(4H, m), 5.6–6.2(2H, m), 6.1–7.3(5H, m) | 25 | — — — | — | — LiI | 180° C. 3 h B |
| 47 | 196 | 1.7–1.9(2H, m), 2.47(2H, t, J=6Hz), 3.22(2H, t, J=5.5Hz), 3.82(3H, s), 3.97(2H, t, J=5.5Hz), 4.16(2H, d, J=5.5Hz), 4.6(1H, br), 5.0–5.3(4H, m), 5.6–6.1(2H, m) | 99 | HCl.salt 93~93.5° C. iPr$_2$O-iPrOH | 208 305 | MeOH NaOMe | 110° C. 15 h A |
| 48 | 197 | 1.7–1.9(2H, m), 2.51(2H, t, J=6Hz), 3.22(2H, t, J=5.5Hz), 3.96(2H, t, J=5.5Hz), 4.16(2H, d, J=5.5Hz), 4.5(1H, br), 4.76(2H, t, J=5.5Hz), 5.0–5.4(4H, m), 5.6–6.7(3H, m) | 75 | HCl.salt | 206 304 | DMF NaH — | 130° C. 15 h B |
| 49 | 198 | 1.7–1.9(2H, m), 2.53(2H, t, J=6Hz), 3.23(2H, t, J=5.5Hz), 3.97(2H, t, J=5.5Hz), 4.17(2H, d, J=5.5Hz), 4.6(1H, br), 5.0–5.3(4H, m), 5.31(2H, s), 5.6–6.1(2H, m), | 74 | fumarate 119~122° C. EtOH | 216 284 | DMF NaH — | 120° C. 13 h A |

| Ex. No. | Compound No. | $^1$H-NMR data of free base (CDCl$_3$) δ(ppm) | Yield of free base (%) | Type of salt M.P. of acid addition salt Recrystallization solvent | UV of acid addition salt EtOH λ$_{max}$ (nm) | Reaction solvent Coexisting base Additive | Reaction temp. Reaction time Reaction vessel (*A: Autoclave B: Atmospheric pressure) |
|---|---|---|---|---|---|---|---|
| 50 | 199 | 7.3–7.4(5H, br) 1.8–2.0(2H, m), 2.47(3H, s), 2.5(2H, t, J=6Hz), 3.24(2H, t, J=5.5Hz), 3.99(2H, t, J=5.5Hz), 4.16(2H, d, J=5.5Hz), 4.5(1H, br), 5.0–5.3(4H, m), 5.6–6.1(2H, m) | 80 | HCl.salt 118~122° C. iPr$_2$O-iPrOH | 225 309 | DMF NaSMe — | 100° C. 15 h B |
| 51 | 200 | 1.2–2.2(13H, m, br), 2.46(2H, t, J=6Hz), 3.22(2H, t, J=5.5Hz), 3.7–3.9(1H, br), 3.97(2H, t, J=5.5Hz), 4.15(2H, d, J=5.5Hz), 4.5(1H, br), 5.0–5.3(4H, m), 5.6–6.1(2H, m) | 95 | fumarate 154~157° C. EtOH | 123 307 | DMF NaH — | 90° C. 2 h B |
| 52 | 202 | 1.7–1.9(2H, m), 2.59(2H, t, J=6Hz), 3.27(2H, t, J=5.5Hz), 3.75(2H, t, J=5.5Hz), 4.16(2H, d, J=5.5Hz), 4.5(1H, br), 5.0–5.3(4H, m), 5.6–6.0(2H, m), 7.2–7.5(4H, m) | 73 | fumarate 153~155.5° C. EtOH | 219 312 | DMF NaH — | 100° C. 4 h B |
| 53 | 203 | 1.72(3H, d, J=7Hz), 1.7–1.95(2H, m), 2.43(2H, t-like, J=6.5Hz), 3.21(2H, t-like, J=5.5Hz), 3.85–4.25(4H, m), 4.5–4.8(1H, br), 4.95–5.35(5H, m), 5.55–6.2(2H, m), 7.15–7.5(5H, m) | 100 | fumarate 113~115° C. EtOH | — | DMF NaH — | 90° C. 1 h B |
| 54 | 204 | 1.7–1.9(2H, m), 2.48(2H, t, J=6Hz), 2.98(2H, t, J=8Hz), 3.24(2H, t, J=5.5Hz), 3.35(2H, t, J=8Hz), 4.02(2H, t, J=5.5Hz), 4.17(2H, d, J=5.5Hz), 4.6(1H, br), 5.0–5.3(4H, m), 5.7–6.1(2H, m), 7.1–7.3(5H, m) | 82 | fumarate 141~144° C. EtOH | 217 307 | DMF NaH — | 100° C. 3 h B |
| 55 | 205 | 1.7–2.0(2H, m), 1.8–2.1(2H, m), 2.48(2H, t, J=6Hz), 2.74(2H, t, J=8Hz), 3.13(2H, t, J=7Hz), 3.23(2H, t, J=5.5Hz), 3.95(2H, t, J=5.5Hz), 4.15(2H, d, J=5.5Hz), 4.5(1H, br), 5.0–5.3(4H, m), 5.6–6.1(2H, m), 7.2(5H, s) | 91 | fumarate 111.5~112.5° C. EtOH | 213 306 | DMF NaH — | 100° C. 3 H B |
| 56 | 209 | 1.7–1.9(2H, m), 2.47(2H, t, J=6Hz), 3.16(4H, t, J=4.5Hz), 3.26(2H, t, J=5.5Hz), 3.76(4H, t, J=4.5Hz), 3.95(2H, t, J=5.5Hz), 4.18(2H, d, J=5.5Hz), 4.6(1H, br), 5.0–5.3(4H, m), 5.6–6.1(2H, m) | 95 | HCl.salt 103~106° C. iPr$_2$O-iPrOH | 219 241 307 | — — LiI | 150° C. 15 h A |
| 57 | 210 | 1.7–1.9(2H, m), 2.45(2H, t, J=6Hz), 2.69(4H, t-like, J=5Hz), 3.26(2H, t, J=5.5Hz), 3.46(4H, t-like, J=5Hz), 3.95(2H, t, J=5.5Hz), 4.18(2H, d, J=5.5Hz), 4.6(1H, br), 5.0–5.3(4H, m), 5.6–6.1(2H, m) | 50 | fumarate 154.5~155° C. EtOH | 217 298 | — — LiI | 160° C. 20 h A |
| 58 | 211 | 1.7–1.9(2H, m), 2.62(2H, t, J=6Hz), 3.36(2H, t, J=5.5Hz), 3.99(2H, t, J=5.5Hz), 4.22(2H, d, J=5.5Hz), 4.5(1H, br), 5.0–5.3(4H, m), 5.6–6.1(2H, m), 7.11(1H, t, J=1Hz), 7.32(1H, m), 7.91(1H, s-like) | 85 | HCl.salt | — | — — — | 140° C. 15 h B |
| 59 | 212 | 1.6–2.0(4H, m), 2.30(2H, t, J=6Hz), 3.20(2H, t, J=5.5Hz), 3.34(2H, t-like), 3.50(2H, t-like), 3.97(2H, t, J=5.5Hz), 4.15(2H, d, J=5.5Hz), 4.3(1H, br), 4.5(1H, br), 5.0–5.3(4H, m), 5.6–6.1(2H, m) | 40 | fumarate EtOH | 212 290 | — — — | 100° C. 6 h B |
| 60 | 213 | 1.7–1.9(2H, m), 2.15–2.25(2H, m), 2.51(2H, t, J=6Hz), 3.26(4H, t, J=5.5Hz), 3.73(2H, br), 3.96(2H, t, J=5.5Hz), 4.19(2H, d, J=5.5Hz), 4.5(1H, br), 5.0–5.3(4H, m), 5.6–6.1(4H, m) | 99 | HCl.salt 102~104° C. Et$_2$O | 218 242 308 | — — LiI | 150° C. 80 h A |
| 61 | 214 | 1.7–1.9(2H, m), 2.57(2H, t, J=6Hz), 2.96(2H, t, J=6Hz), 3.28(2H, t, J=5.5Hz), 3.45(2H, t, J=6Hz), 3.98(2H, t, J=5.5Hz), 4.19(2H, d, J=5.5Hz), 4.40(2H, s), 4.6(1H, br), 5.0–5.3(4H, m), 5.6–6.1(2H, m), 7.12(4H, s) | 93 | fumarate 119~125° C. EtOH | 215 299 | — — — | 150° C. 15 h A |
| 62 | 215 | 1.7–1.9(2H, m), 2.84(2H, t, J=6Hz), 3.40(2H, t, J=5.5Hz), 4.04(2H, t, J=5.5Hz), 4.29(2H, d, J=5.5Hz), 4.9(1H, br), 5.0–5.3(4H, m), 5.7–6.1(2H, m), 7.3–7.6(2H, m), 8.0–8.15(2H, m) | 41 | HCl.salt | 225 255 288 | DMF NaH LiI | 150° C. 30 h B |
| 63 | 216 | 1.7–1.9(2H, m), 2.3–2.5(6H, m, br), 2.52(3H, s), 3.22(4H, t, J=5Hz), 3.29(2H, t, J=5.5Hz), 4.13(2H, d, J=5.5Hz), 4.25(1H, s), 5.0–5.2(2H, m), 5.7–6.1(1H, m), 6.97(4H, t, J=9Hz), 7.25–7.45(4H, m) | 25 | — | — | DMF — LiI | 110° C. 30 h B |
| 64 | 217 | 1.7–1.9(2H, m), 2.4(6H, br), 3.00(3H, s), 3.2(6H, br), 4.1–4.25(5H, m), 5.0–5.2(4H, m), 5.6–6.1(2H, m), 6.95(4H, t, J=9Hz), 7.25–7.45(4H, m) | 60 | — | — | — — LiI | 160° C. 20 h B |
| 65 | 218 | 1.7–1.9(2H, m), 2.47(6H, t, J=5Hz), 3.18(4H, t, J=5Hz), 3.24(2H, t, J=5.5Hz), 4.11(4H, d, J=5.5Hz), 4.16(2H, d, J=5.5Hz), 4.23(1H, s), 5.0–5.2(6H, m), 5.6–6.1(3H, m), 6.96(4H, t, J=9Hz), 7.25–7.45(4H, s) | 65 | — | — | — — LiI | 160° C. 20 h B |
| 66 | 223 | 1.66(3H, s), 1.7–1.9(2H, m), 2.43(6H, t-like, J=5.5Hz), 3.19(4H, t, J=5Hz), 3.24(2H, br), 3.94(2H, t, J=5.5Hz), 4.16(2H, s), 4.24(1H, s), 4.6(1H, br), 4.8(2H, br), 5.03(1H, dd, J=2&15Hz), 5.12(1H, dd, J=2&15Hz), 6.95(4H, t, J=9Hz), 7.25–7.45(4H, m) | 65 | HCl.salt 145~170° C. (dec.) iPr$_2$O | 205 243 309 | — — LiI | 130° C. 15 h A |
| 67 | 224 | 1.65(3H, s), 1.74(3H, s), 1.7–1.9(2H, m), 2.43(6H, t-like, J=5.5Hz), 3.18(6H, t-like, J=5Hz), 3.89(2H, t, J=5.5Hz), 4.15(2H, s), 4.24(1H, s), 4.6(1H, br), 4.7–4.9(4H, m, br), 6.95(4H, t, J=9Hz), 7.2–7.45(4H, m) | 55 | HCl.salt 124~128° C. iPr$_2$O | 205 243 310 | — — LiI | 140° C. 20 h A |
| 68 | 230 | 1.7–1.9(2H, br), 2.43(6H, t-like, J=5.5Hz), | 60 | HCl.salt | 206 | — | 170° C. |

-continued

| Ex. No. | Compound No. | $^1$H-NMR data of free base (CDCl$_3$) δ(ppm) | Yield of free base (%) | Type of salt M.P. of acid addition salt Recrystallization solvent | (*A: Autoclave B: Atmospheric pressure) UV of acid addition salt EtOH $\lambda_{max}$ (nm) | Reaction solvent Coexisting base Additive | Reaction temp. Reaction time Reaction vessel |
|---|---|---|---|---|---|---|---|
| | | 3.18(4H, t, J=5Hz), 3.25(2H, br), 3.94(2H, t, J=5.5Hz), 4.25(1H, s), 4.6(1H, br), 4.81(2H, s), 5.0–5.2(2H, m), 5.7–6.1(1H, m), 6.96(4H, t, J=9Hz), 7.2–7.4(4H, m), 7.25(5H, s) | | 154~157° C. iPr$_2$O | 245 310 | — LiI — | 20 h B |
| 69 | 233 | 1.7–2.0(2H, m), 2.30(2H, t-like, J=5.7Hz), 3.15(2H, t-like, J=5.2Hz), 3.8–4.2(5H, m), 4.4(1H, br), 4.80(2H, s), 4.85–5.4(4H, m), 5.7–6.2(2H, m), 7.25(5H, s) | 43 | HCl.salt 130~137° C. EtOH | 292 215 | — LiI — | 140° C. 20 h B |
| 70 | 234 | 1.7–1.9(2H, br), 2.43(6H, t-like, J=5.5Hz), 3.19(4H, t, J=5Hz), 3.24(2H, t, J=5.5Hz), 4.25(1H, s), 4.6(1H, t-like, br), 4.50(2H, d, J=6Hz), 4.78(2H, s), 6.96(4H, t, J=9Hz), 7.2–7.45(14H, m) | 65 | — | — | — LiI | 170° C. 20 h B |
| 71 | 235 | 1.7–1.9(2H, br), 2.4(6H, t-like, J=5.5Hz), 2.46(3H, s), 3.1–3.4(6H, br), 4.25(1H, s), 4.77(2H, s), 6.96(4H, t, J=9Hz), 7.24(5H, s), 7.25–7.45(4H, m) | 30 | — | — | — — LiI | 140° C. 10 h B |
| 72 | 240 | 1.7–2.1(2H, m), 2.2–2.5(2H, m), 2.87(2H, dd, J=8&6Hz), 3.1–3.35(2H, m), 3.73(2H, dd, J=8&6Hz), 3.9–4.3(6H, m), 4.95–5.4(4H, m), 5.7–6.3(2H, m), 7.23(5H, s) | 30 | fumarate 190~197° C. EtOH | — | — LiI | 170° C. 22 h A |
| 73 | 242 | 1.8–2.1(2H, m), 2.30(2H, t-like, J=6.8Hz), 3.24(2H, t-like, J=4.4Hz), 3.9–4.7(8H, m), 5.0–5.4(4H, m), 5.8–6.6(4H, m), 7.2–7.5(5H, m) | 20 | — | — | — LiI | 170° C. 14 h A |
| 74 | 244 | 1.7–1.9(2H, br), 2.35–2.55(6H, br), 2.48(3H, s), 2.53(3H, s), 3.38(4H, t, J=5Hz), 3.77(2H, t, J=5.5Hz), 4.25(1H, s), 6.98(4H, t, J=9Hz), 7.2–7.45(4H, m) | 15 | — | — | DMF — | 120° C. 10 h B |

Example 75: Effect on Partial Pressure Value of Gases in Arterial Blood (Intravenous Injection System)

Method A

Male Wistar strain rats (body weight about 300 g) were anesthetized intra-peritonealy with urethane, and a cannula was inserted into the respiratory tract and the femoral artery, respectively. A suspension (30–100 μm, 10 mg/ml) of carbon powder in a corn oil was intratrachealy injected to induce a hypoxemia state (PaO$_2$: 50–60 mmHg). A compound in the present invention was continuously injected into these hypoxemia model animals intravenously (0.1 mg/kg/min, 10 min), and then a partial pressure value of gases (PaO$_2$, PaCO$_2$) in arterial blood was immediately determined.

Method B

Male Wistar strain rats (body weight about 300 g) were anesthetized with halothane inhalant, and then 2.0% acetic acid was intratrachealy injected at 0.6 ml/kg to induce a respiratory insufficiency. The animals were intraperitonealy anesthetized with urethane-α-chloralose, and a cannula was inserted into the femoral artery. After the hypoxemic state (PaO$_2$: 60–70 mmHg) was observed a compound in accordance with the present invention (test substance) was continuously injected into these hypoxemia model animals intravenously (0.1 mg/kg/min, 10 min), and then a partial pressure value of gases (PaO$_2$, PaCO$_2$) in arterial blood was immediately determined.

The results are as shown in Table 1.

TABLE 1

Activity for Increasing PaO$_2$ and Decreasing PaCO$_2$ by Intravenous Injection

| Test Compound | Method | PaO$_2$ Increasing Activity ΔPaO$_2$ | PaCO$_2$ Decreasing Activity ΔPaCO$_2$ |
|---|---|---|---|
| 112 | A | +4.6 | −2.0 |
| 121 | B | +15.9 | −1.2 |
| 143 | B | +8.1 | −0.7 |
| 145 | B | +11.2 | −0.8 |
| 146 | B | +6.6 | +2.5 |
| 153 | B | +10.0 | −0.9 |
| 155 | B | +6.6 | +2.6 |
| 159 | A | +4.8 | +0.4 |
| 168 | B | +14.4 | −12.2 |
| 171 | B | +17.4 | −13.4 |
| 184 | B | +10.4 | −3.2 |
| 189 | B | +16.0 | −7.6 |
| 203 | B | +9.5 | −2.1 |
| 204 | B | +15.0 | +2.2 |
| 209 | B | +7.6 | −2.4 |
| 213 | B | +10.3 | −2.9 |
| 214 | B | +9.8 | +2.2 |
| 233 | B | +8.6 | −4.0 |

Unit: mmHg
(indication of activity)
ΔPaO$_2$ = (PaO$_2$ after administration - PaO$_2$ before administration) for test compound
ΔPaCO$_2$ = (PaCO$_2$ after administration - PaCO$_2$ before administration) for test compound Example 76: Effect on Partial Pressure Value of Gases in Arterial Blood (Oral Administration System)

Male Wistar strain rats (body weight about 250 g) fasted overnight were anesthetized with halothane inhalant, and then a cannula was inserted into the femoral artery. After the animals recovered from the anesthesia, they were again anesthetized with halothane inhalant, and then 2.0% acetic acid was intratrachealy injected at 0.8 ml/kg to induce a hypoxemia state. After the hypoxemic state was observed over about 60 min., a compound in accordance with the present invention (test substance) was orally administered to the animals. On 60 min. after the administration, the partial pressure value of gases (PaO$_2$, PaCO$_2$) in arterial blood was determined.

The results are as shown in Table 2.

TABLE 2

Activity for Increasing PaO$_2$ and Decreasing PaCO$_2$ by Oral Administration

| Test Compound | PaO$_2$ Increasing Activity ΔPaO$_2$ | PaCO$_2$ Decreasing Activity ΔPaCO$_2$ |
|---|---|---|
| 121 | ++ | + |
| 143 | + | ± |
| 145 | + | ± |
| 155 | ++ | + |
| 171 | + | ± |
| 209 | + | + |

(Indication of activity)
ΔPaO$_2$ = (PaO$_2$ after administration - PaO$_2$ before administration) of test compound
ΔPaCO$_2$ = (PaCO$_2$ after administration - PaCO$_2$ before administration) of test compound
ΔPaO$_2$
+: +3–+6 mmHg
++: +6–+9 mmHg
ΔPaCO$_2$
±: 0—–3 mmHg
+: –3—–6 mmHg
++: –6—–9 mmHg

Example 77: Preparation of Tablet

A tablet containing 30 mg of the compound prepared in Example 1 was prepared as follows:

| | |
|---|---|
| Compound prepared in Ex. 1 | 30 mg |
| Lactose | 87 mg |
| Starch | 30 mg |
| Magnesium stearate | 3 mg |

Example 78: Preparation of Injection

A solution for injection containing 0.3 mg, based on 1 ml of the solution, of the compound prepared in Example 1 was prepared according to the following formulation.

| | |
|---|---|
| Compound prepared in Ex. 1 | 30 mg |
| Sodium chloride | 900 mg |
| Distilled water for injection | 100 ml |

INDUSTRIAL APPLICABILITY

The compounds in the present invention, and pharmaceutical preparations thereof, are particularly useful for the treatment of hypoxemia associated with respiratory diseases, and further, an effective process for preparing of same is provided.

We claim:

1. A fused pyrimidine derivative represented by formula (I):

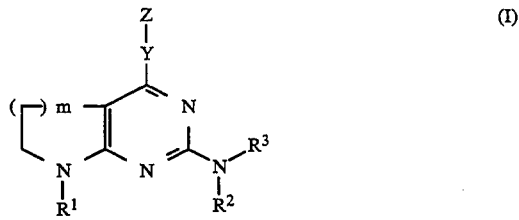

wherein:

R$^1$ represents a hydrogen atom, or an unsubstituted or substituted alkyl, alkenyl, arylalkyl, arylalkenyl or alkylcarbonyl group;

R$^2$ and R$^3$ independently of each other represent a hydrogen atom, or an unsubstituted or substituted alkyl, alkenyl, arylalkyl, arylalkenyl or alkylcarbonyl group; or R$^2$ and R$^3$ are optionally taken together with the adjacent nitrogen atom to form an unsubstituted saturated 5- to 7- membered ring, which may be constructed with one or two hetero atoms selected from the group consisting of N, O and S, with the proviso that either R$^2$ or R$^3$ represents a group other than a hydrogen atom;

Y represents a linking group of the formula

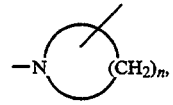

wherein n is an integer of from 4 to 6,

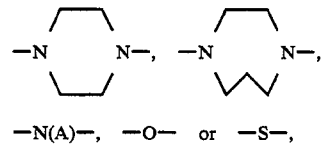

—N(A)—, —O— or —S—, wherein A is a hydrogen atom or alkyl group; and

Z, when bonded to a carbon atom on the linking group, represents a hydrogen atom, or carboxylic, amino or hydroxyl group, or an unsubstituted or substituted alkyl, aryl, arylalkyl, alkyloxy, alkylcarbonyloxy, alkyloxycarbonyl, arylcarbonyloxy, arylalkylcarbonyloxy, arylalkenylcarbonyloxy, alkylamino, alkenylamino, arylamino, arylalkylamino or alkylcarbonylamino group; and when bonded to an atom other than said carbon atom of the linking group, represents a hydrogen atom, or an unsubstituted or substituted alkyl, alkenyl, aryl, arylalkyl, arylalkenyl, alkylcarbonyl, arylalkylcarbonyl, arylalkenylcarbonyl or arylcarbonyl group; or Y and Z together represent an unsubstituted or substituted alkyl, alkenyl or arylalkyl group; or a 5- to 7-member heterocyclic ring which has a nitrogen atom, and further, an oxygen or sulfur atom as a hetero atom other than the nitrogen atom, being bonded via the nitrogen atom therein to the 4-position of the pyrimidine ring of the formula (I), a 5- to 7- member unsaturated heterocyclic ring which has 1 to 3 nitrogen atoms being bonded via the nitrogen atom therein to the 4-position of the pyrimidine ring of the formula (I), or a fused biheterocyclic ring, constructed with 5- or 6- membered aromatic or non-aromatic rings, which has 1 to 3 nitrogen atoms in any position, being bonded via the nitrogen atom therein to the 4-position of the pyrimidine ring of the formula (I);

m is an integer of from 1 to 3; and in said substituted alkyl, alkenyl, aryl, arylalkyl, arylalkenyl, alkylcarbonyl, arylcarbonyl, arylalkylcarbonyl, arylalkenylcarbonyl, alkylcarbonyloxy, alkyloxycarbonyl, arylcarbonyloxy, arylalkylcarbonyloxy, arylalkenylcarbonyloxy, alkylamino, arylamino, arylalkylamino and alkylcarbonylamino groups, the substituent represents an alkyl, halogenated alkyl, alkyloxy, alkylcarbonyloxy, hydroxyl, amino, nitro or cyano group, or a halogen atom, which is bonded to a chain or ring moiety in said substituted groups, or alkylene group being taken together with a carbon atom in the chain moiety to form a ring; and a pharmaceutically acceptable acid addition salt thereof.

2. A pharmaceutical preparation comprising a pharmaceutical carrier and a derivative, or an acid addition salt thereof, of a fused pyrimidine derivative represented by the following formula (I):

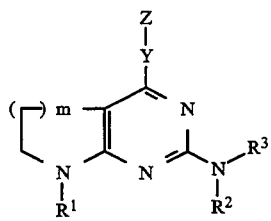

(I)

wherein:

R$^1$ represents a hydrogen atom, or an unsubstituted or substituted alkyl, alkenyl, arylalkyl, arylalkenyl or alkylcarbonyl group;

R$^2$ and R$^3$, independently of each other, represent a hydrogen atom, or an unsubstituted or substituted alkyl, alkenyl, arylalkyl, arylalkenyl or alkylcarbonyl group; or R$^2$ and R$^3$ are optionally taken together with the adjacent nitrogen atom to form an unsubstituted saturated 5- to 7- membered ring, which may be constructed with one or two hetero atoms selected from the group consisting of N, O and S, with the proviso that either R$^2$ or R$^3$ represents a group other than a hydrogen atom;

Y represents a linking group of the formula

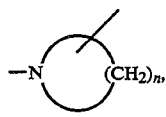

wherein n is an integer of from 4 to 6

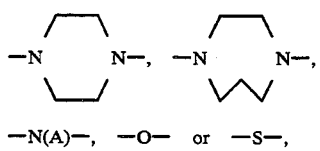

—N(A)—, —O— or —S—, wherein A is a hydrogen atom or alkyl group; and

Z, when bonded to a carbon atom on the linking group, represents a hydrogen atom, or carboxylic, amino or hydroxyl group, or an unsubstituted or substituted alkyl, aryl, arylalkyl, alkyloxy, alkylcarbonyloxy, alkyloxycarbonyl, arylcarbonyloxy, arylalkylcarbonyloxy, arylalkenylcarbonyloxy, alkylamino, alkenylamino, arylamino, arylalkylamino or alkylcarbonylamino group; and when bonded to an atom other than said carbon atom of the linking group, represents a hydrogen atom, or an unsubstituted or substituted alkyl, alkenyl, aryl, arylalkyl, arylalkenyl, alkylcarbonyl, arylalkylcarbonyl, arylalkenylcarbonyl or arylcarbonyl group; or Y and Z together represent an unsubstituted or substituted alkyl, alkenyl or arylalkyl group; or a 5- to 7-member heterocyclic ring which has a nitrogen atom, and further, an oxygen or sulfur atom as a hetero atom other than the nitrogen atom, being bonded via the nitrogen atom therein to the 4-position of the pyrimidine ring of the formula (I), a 5- to 7- member unsaturated heterocyclic ring which has 1 to 3 nitrogen atoms being bonded via the nitrogen atom therein to the 4-position of the pyrimidine ring of the formula (I), or a fused biheterocyclic ring constructed with 5- or 6- membered aromatic or non-aromatic rings, which has 1 to 3 nitrogen atoms in any position, being bonded via the nitrogen atom therein to the 4-position of the pyrimidine ring of the formula (I);

m is an integer of from 1 to 3; and in said substituted alkyl, alkenyl, aryl, arylalkyl, arylalkenyl, alkylcarbonyl, arylcarbonyl, arylalkylcarbonyl, arylalkenylcarbonyl, alkylcarbonyloxy, alkyloxycarbonyl, arylcarbonyloxy, arylalkylcarbonyloxy, arylalkenylcarbonyloxy, alkylamino, arylamino, arylalkylamino and alkylcarbonylamino groups, the substituent represents an alkyl, halogenated alkyl, alkyloxy, alkylcarbonyloxy, hydroxyl, amino, nitro or cyano group, or a halogen atom, which is bonded to a chain or ring moiety in said substituted groups, or alkylene group being taken together with a carbon atom in the chain moiety to form a ring; and a pharmaceutically acceptable acid addition salt thereof.

3. A method for treating hypoxemia associated with a respiratory disease by using a pharmaceutically effective amount of a pharmaceutical preparation comprising a derivative, or an acid addition salt thereof, of a fused pyrimidine derivative represented by the following formula (I):

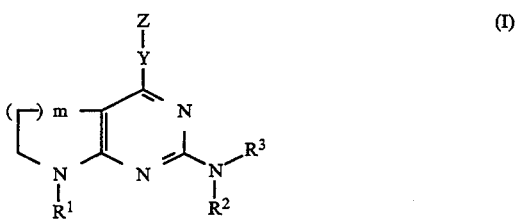

(I)

wherein:

R$^1$ represents a hydrogen atom, or an unsubstituted or substituted alkyl, alkenyl, arylalkyl, arylalkenyl or alkylcarbonyl group;

R$^2$ and R$^3$, independently of each other, represent a hydrogen atom, or an unsubstituted or substituted alkyl, alkenyl, arylalkyl, arylalkenyl or alkylcarbonyl group; or $R^2$ and $R^3$ are optionally taken together with the adjacent nitrogen atom to form an unsubstituted saturated 5- to 7- membered ring, which may be constructed with one or two hetero atoms selected from the group consisting of N, O and S, with the proviso that either $R^2$ or $R^3$ represents a group other than a hydrogen atom;

Y represents a linking group of the formula

wherein n is an integer of from 4 to 6,

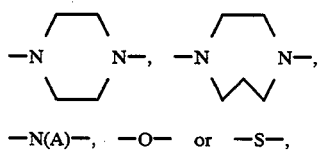

wherein A is a hydrogen atom or alkyl group; and

Z, when bonded to a carbon atom on the linking group, represents a hydrogen atom, or carboxylic, amino or hydroxyl group, or an unsubstituted or substituted alkyl, aryl, arylalkyl, alkyloxy, alkylcarbonyloxy, alkyloxycarbonyl, arylcarbonyloxy, arylalkylcarbonyloxy, arylalkenylcarbonyloxy, alkylamino, alkenylamino, arylamino, arylalkylamino or alkylcarbonylamino group; and when bonded to an atom other than said carbon atom of the linking group, represents a hydrogen atom, or an unsubstituted or substituted alkyl, alkenyl, aryl, arylalkyl, arylalkenyl, alkylcarbonyl, arylalkylcarbonyl, arylalkenylcarbonyl or arylcarbonyl group; or Y and Z together represent an unsubstituted or substituted alkyl, alkenyl or arylalkyl group; or a 5- to 7-member heterocyclic ring which has a nitrogen atom, and further, an oxygen or sulfur atom as a hetero atom other than the nitrogen atom, being bonded via the nitrogen atom therein to the 4-position of the pyrimidine ring of the formula (I), a 5- to 7- member unsaturated heterocyclic ring which has 1 to 3 nitrogen atoms being bonded via the nitrogen atom therein to the 4-position of the pyrimidine ring of the formula (I), or a fused biheterocyclic ring constructed with 5- or 6- membered aromatic or non-aromatic rings, which has 1 to 3 nitrogen atoms in any position, being bonded via the nitrogen atom therein to the 4-position of the pyrimidine ring of the formula (I);

m is an integer of from 1 to 3; and in said substituted alkyl, alkenyl, aryl, arylalkyl, arylalkenyl, alkylcarbonyl, arylcarbonyl, arylalkylcarbonyl, arylalkenylcarbonyl, alkylcarbonyloxy, alkyloxycarbonyl, arylcarbonyloxy, arylalkylcarbonyloxy, arylalkenylcarbonyloxy, alkylamino, arylamino, arylalkylamino and alkylcarbonylamino groups, the substituent represents an alkyl, halogenated alkyl, alkyloxy, alkylcarbonyloxy, hydroxyl, amino, nitro or cyano group, or a halogen atom, which is bonded to a chain or ring moiety in said substituted groups, or alkylene group being taken together with a carbon atom in the chain moiety to form a ring; and a pharmaceutically acceptable acid addition salt thereof.

4. A derivative and pharmaceutically acceptable acid addition salt thereof in accordance with claim 1, wherein m is an integer of 2.

5. A derivative and pharmaceutically acceptable acid addition salt thereof in accordance with claim 1, wherein $R^1$ is selected from the group consisting of an unsubstituted or substituted alkyl, alkenyl and arylalkyl group; and $R^2$ and $R^3$ are selected from the group consisting of one of them being a hydrogen atom and another being an unsubstituted or substituted alkyl or alkenyl group.

6. A derivative and pharmaceutically acceptable acid addition salt thereof in accordance with claim 1, wherein Y represents a linking group of the formula

wherein n is an integer of from 4 to 6,

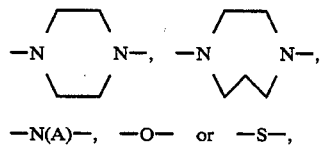

wherein A is a hydrogen atom or alkyl group; and Z, when bonded to a carbon atom on the linking group, is selected from the group consisting of a hydrogen atom, a hydroxyl group, and unsubstituted or substituted alkyl, aryl, arylalkyl, alkyloxy, alkylcarbonyloxy, alkyloxycarbonyl, alkylamino and arylalkylamino groups; and when bonded to an atom other than said carbon atom of the linking group, is selected from the group consisting of a hydrogen atom, and an unsubstituted or substituted alkyl, alkenyl, aryl, arylalkyl, arylalkenyl, alkenylamino and arylcarbonyl, or Y and Z together represent an unsubstituted or substituted alkenyl or arylalkyl group; or a 5- to 7- member heterocyclic ring which has a nitrogen atom, and further an oxygen or sulfur atom as a hetero atom other than the nitrogen atom, being bonded via the nitrogen atom therein to the 4-position of the pyrimidine ring of the formula (I), a 5- to 7- member unsubstituted heterocyclic ring which has 1 to 3 nitrogen atoms, being bonded via the nitrogen atom therein to the 4-position of the pyrimidine ring, constructed with 5- or 6-membered aromatic or non-aromatic rings, of the formula (I), or a fused biheterocyclic ring, constructed with 5- or 6- membered aromatic or non-aromatic rings, which has 1 to 3 nitrogen atoms in any position, being bonded via the nitrogen atom therein to the 4-position of the pyrimidine ring of the formula (I).

7. A derivative and pharmaceutically acceptable acid addition salt thereof in accordance with claim 4, wherein $R^1$ is selected from the group consisting of methyl, cyclopropylmethyl, allyl, 2-methylallyl, benzyl, 1-phenylethyl and 2-phenylethyl groups; $R^2$ and $R^3$ are selected from the group consisting of one thereof being a hydrogen atom and another being selected from the group consisting of methyl, allyl and 2-methylallyl groups; Y is selected from the group consisting of the linking groups represented by the formulae

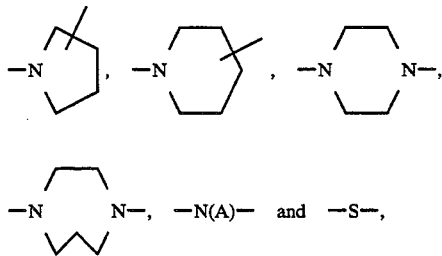

wherein A is a hydrogen atom, or methyl or ethyl group; and Z, when bonded to the carbon atom, is selected from the group consisting of a hydrogen atom, and unsubstituted or substituted aryl and alkylcarbonyloxy groups, and when bonded to an atom other than said carbon atom, is selected from the group consisting of a hydrogen atom, and unsubstituted or substituted alkyl, alkenyl, aryl, and arylalkyl groups; or —Y—Z is selected from the group consisting of the formulae:

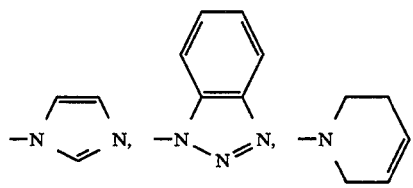

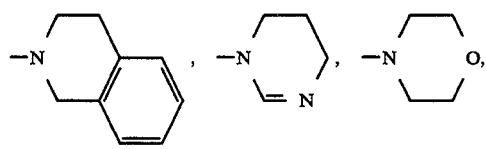

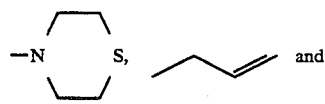

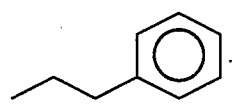

8. A derivative and pharmaceutically acceptable acid addition salt thereof in accordance with claim 4, wherein R¹ is selected from the group consisting of methyl, allyl and 2-methylallyl; R² and R³ are selected from the group consisting of one thereof being a hydrogen atom and another being selected from the group consisting of allyl and 2-methylallyl; and Y is a linking group represented by the formula

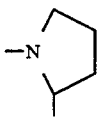

and Z is a hydrogen atom; or Y is a linking group represented by the formula

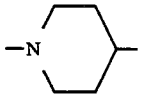

and Z is selected from the group consisting of a hydrogen atom, and phenyl and acetyloxy groups; or Y is a linking group represented by the formula

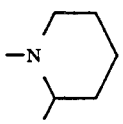

and Z is a hydrogen atom; or Y is a linking group represented by the formula

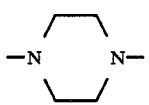

and Z is selected from the group consisting of a hydrogen atom, and unsubstituted or substituted alkyl and arylalkyl groups; or Y is a linking group represented by the formula

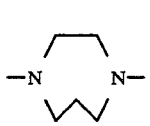

and Z is a methyl group; or Y is a linking group represented by the formula —N(A)—, wherein A is a hydrogen atom or methyl group, and Z is selected from the group consisting of unsubstituted or substituted alkyl, alkenyl and arylalkyl groups; or Y is a linking group represented by the formula —S— and Z is selected from the group consisting of cyclohexyl, 1-phenylethyl and 2-phenylethyl groups; or —Y—Z is selected from the group consisting of the formulae

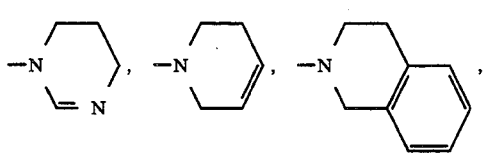

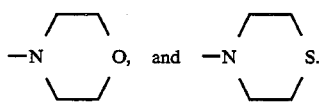

* * * * *